(12) United States Patent
Schmitz

(10) Patent No.: US 8,959,744 B2
(45) Date of Patent: Feb. 24, 2015

(54) MANUFACTURING METHOD FOR THE MAKING OF ARTICLES OR PRECURSORS COMPRISING HOOPS

(76) Inventor: Christoph Schmitz, Euskirchen (DE)

( * ) Notice: Subject to any disclaimer, the term of this patent is extended or adjusted under 35 U.S.C. 154(b) by 610 days.

(21) Appl. No.: 12/998,702

(22) PCT Filed: Aug. 11, 2009

(86) PCT No.: PCT/EP2009/005814
§ 371 (c)(1),
(2), (4) Date: Jun. 14, 2011

(87) PCT Pub. No.: WO2010/057543
PCT Pub. Date: May 27, 2010

(65) Prior Publication Data
US 2012/0042493 A1 Feb. 23, 2012

(30) Foreign Application Priority Data
Nov. 18, 2008 (GB) ................... 0821022.1

(51) Int. Cl.
*B21D 39/03* (2006.01)
*A61F 13/15* (2006.01)
*A61F 13/496* (2006.01)
*A61F 13/62* (2006.01)

(52) U.S. Cl.
CPC ..... *A61F 13/15756* (2013.01); *A61F 13/15804* (2013.01); *A61F 13/496* (2013.01); *A61F 13/62* (2013.01)
USPC ........................................ 29/430

(58) Field of Classification Search
USPC .............. 29/430, 428, 426.1, 426.4; 604/358; 156/257
See application file for complete search history.

(56) References Cited

U.S. PATENT DOCUMENTS

| | | | |
|---|---|---|---|
| 4,134,154 A | 1/1979 | Faulkner | |
| 4,975,140 A | 12/1990 | Kang | |
| 6,098,557 A | 8/2000 | Couillard et al. | |
| 6,681,406 B2 | 1/2004 | Yang | |
| 6,926,702 B1 | 8/2005 | Wilkinson | |
| 2005/0145150 A1 | 7/2005 | Mortell | |

FOREIGN PATENT DOCUMENTS

| | | |
|---|---|---|
| EP | 1224875 A1 | 7/2002 |
| EP | 1428487 A1 | 6/2004 |
| WO | WO 2006/102973 A1 | 10/2006 |
| WO | WO 2006/102974 A1 | 10/2006 |
| WO | WO 2006/103487 A1 | 10/2006 |
| WO | WO 2008/037281 A1 | 4/2008 |

*Primary Examiner* — John C Hong

(57) ABSTRACT

The present invention relates to processes for the manufacture of hoops and pre-forms for making articles comprising such hoops such as pants or a pants-like structures, such as baby or incontinence diapers, absorbent pants such as training, feminine hygiene or adult incontinent pants, or garments like underwear, such as reusable or single use pants, exhibiting particularly good body conforming fit.

8 Claims, 38 Drawing Sheets

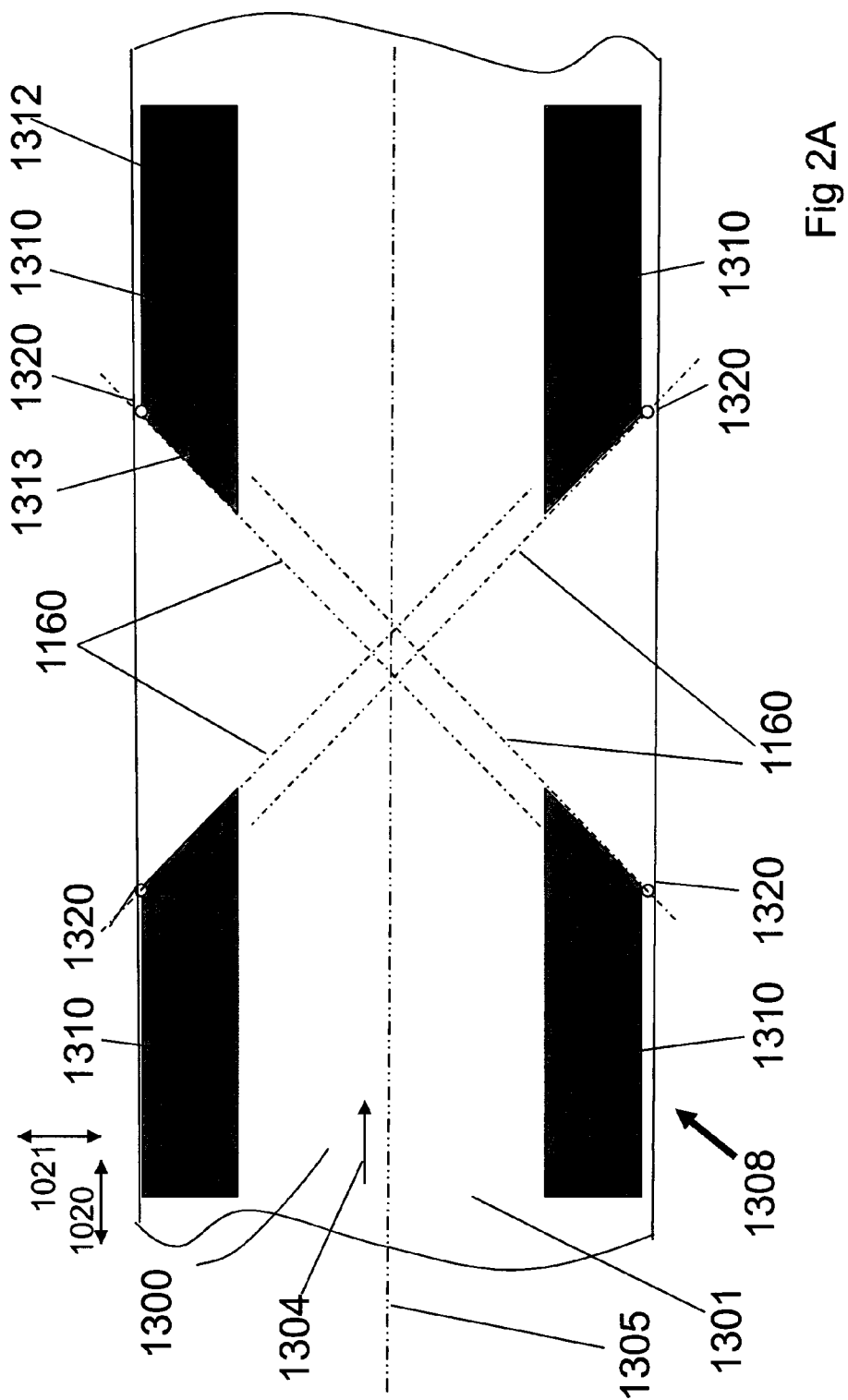

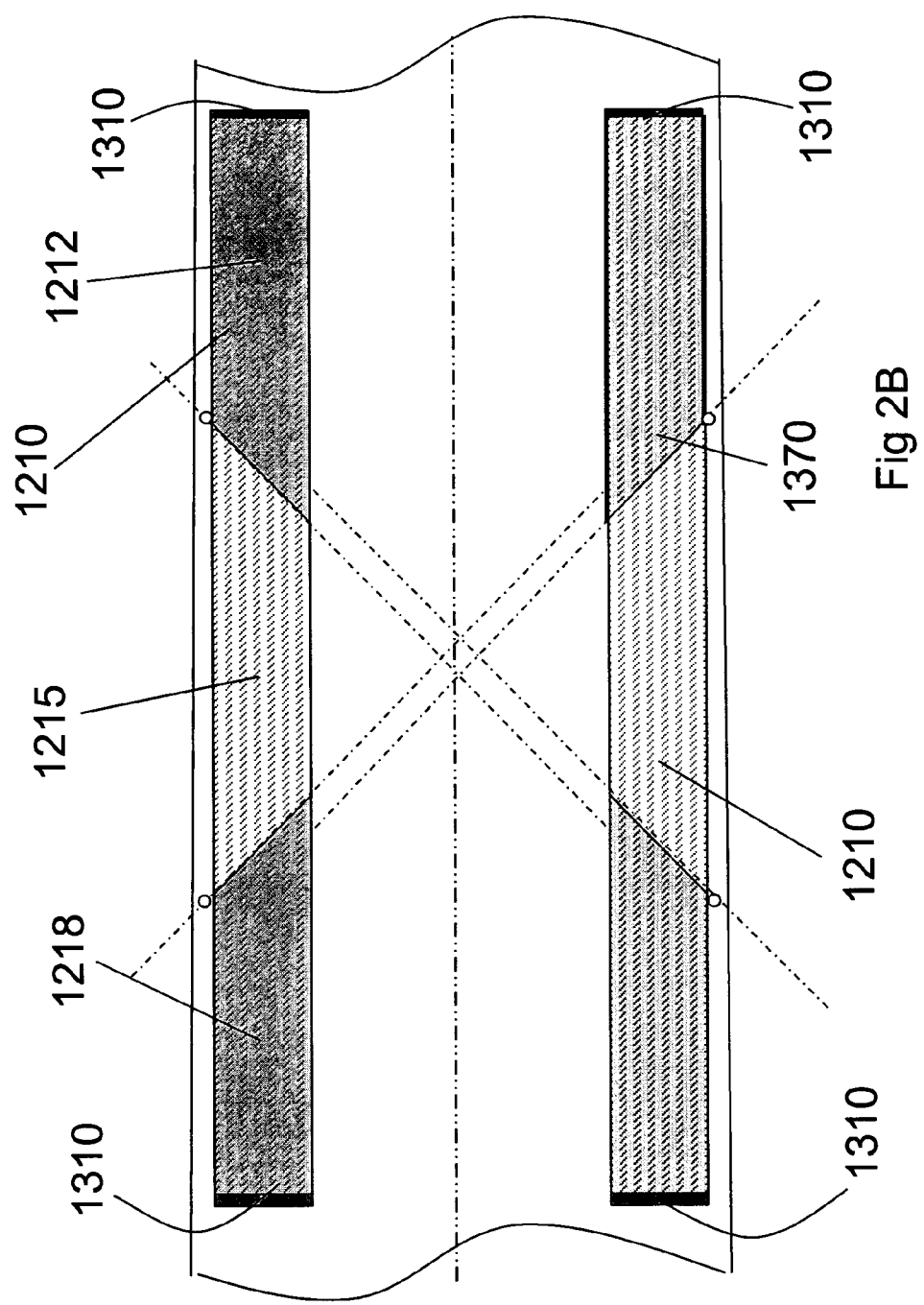

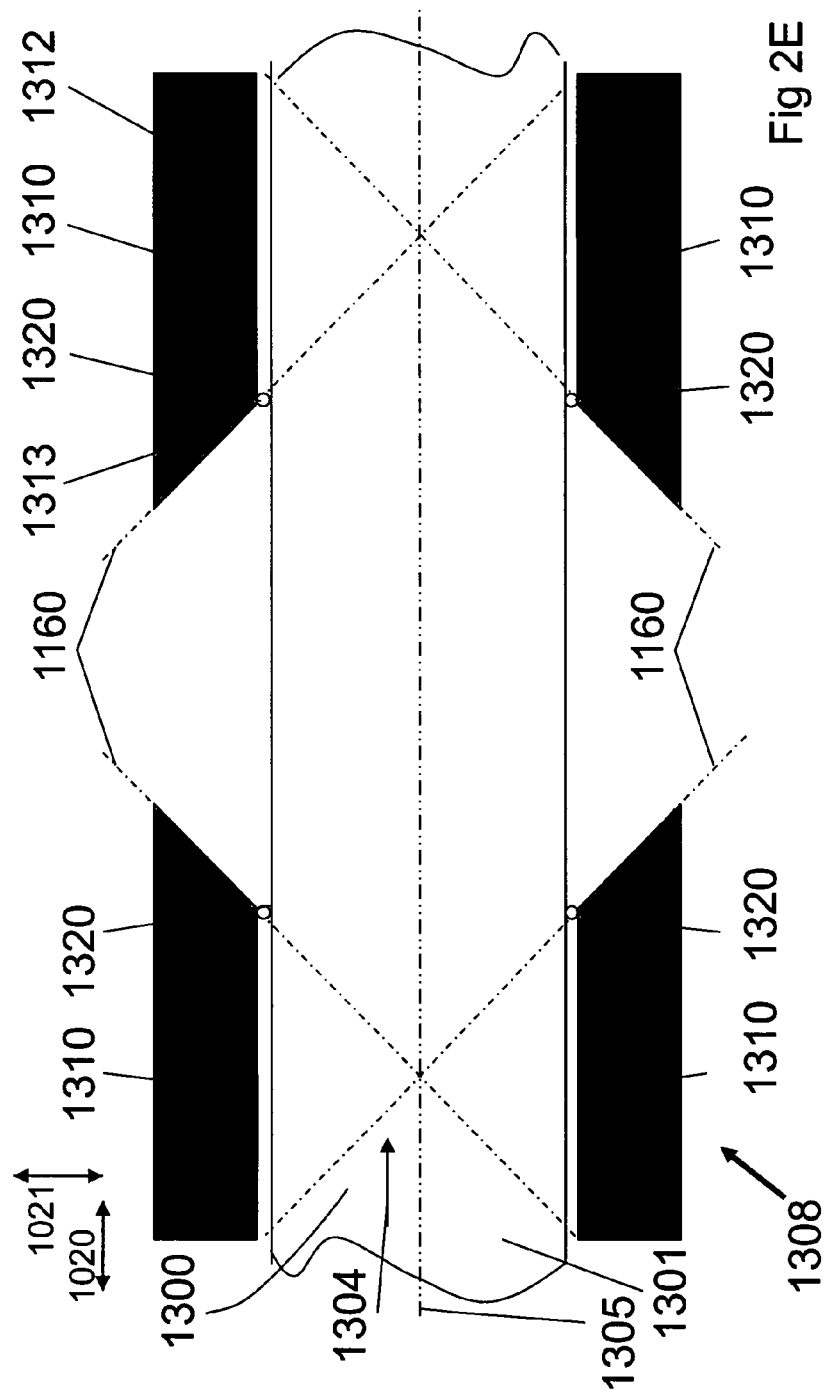

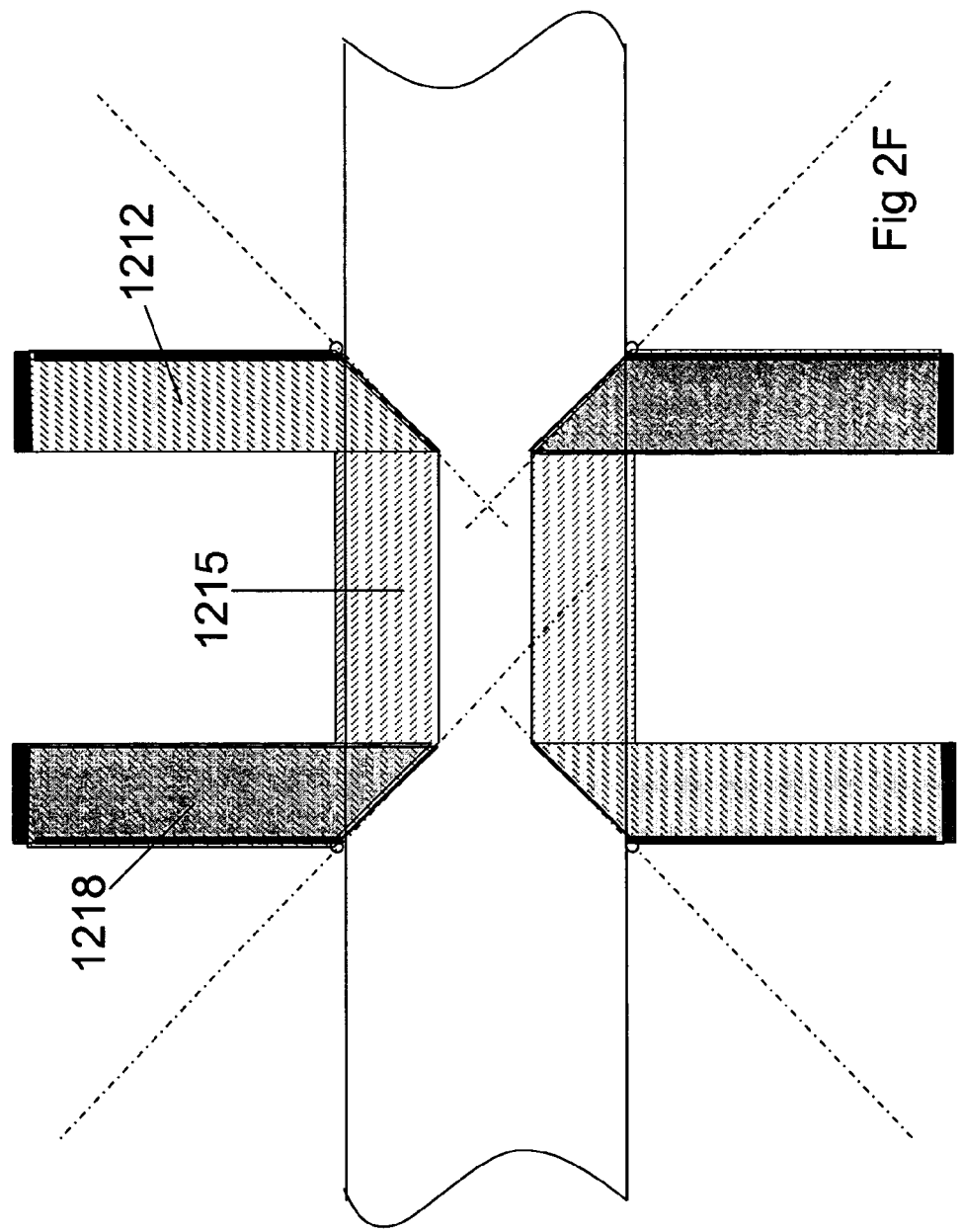

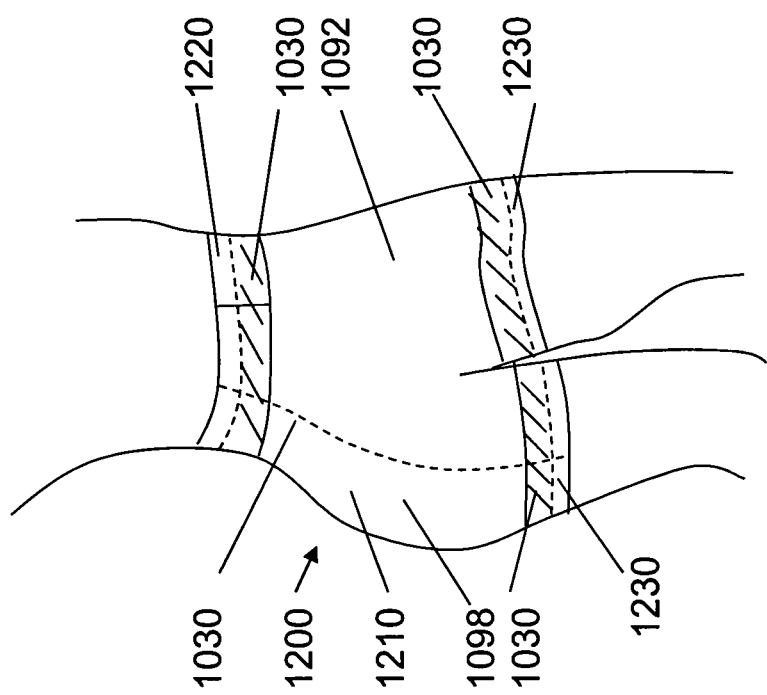

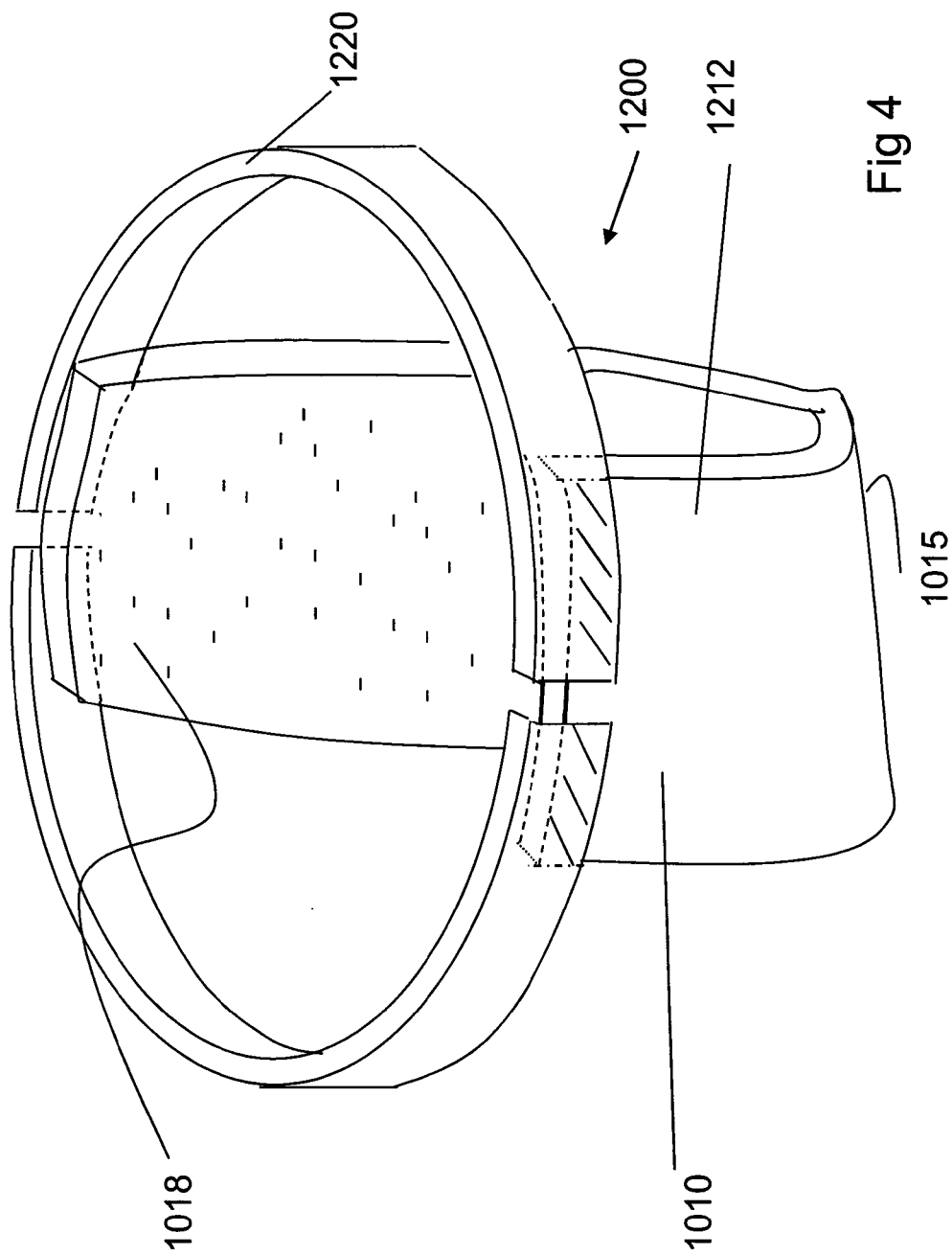

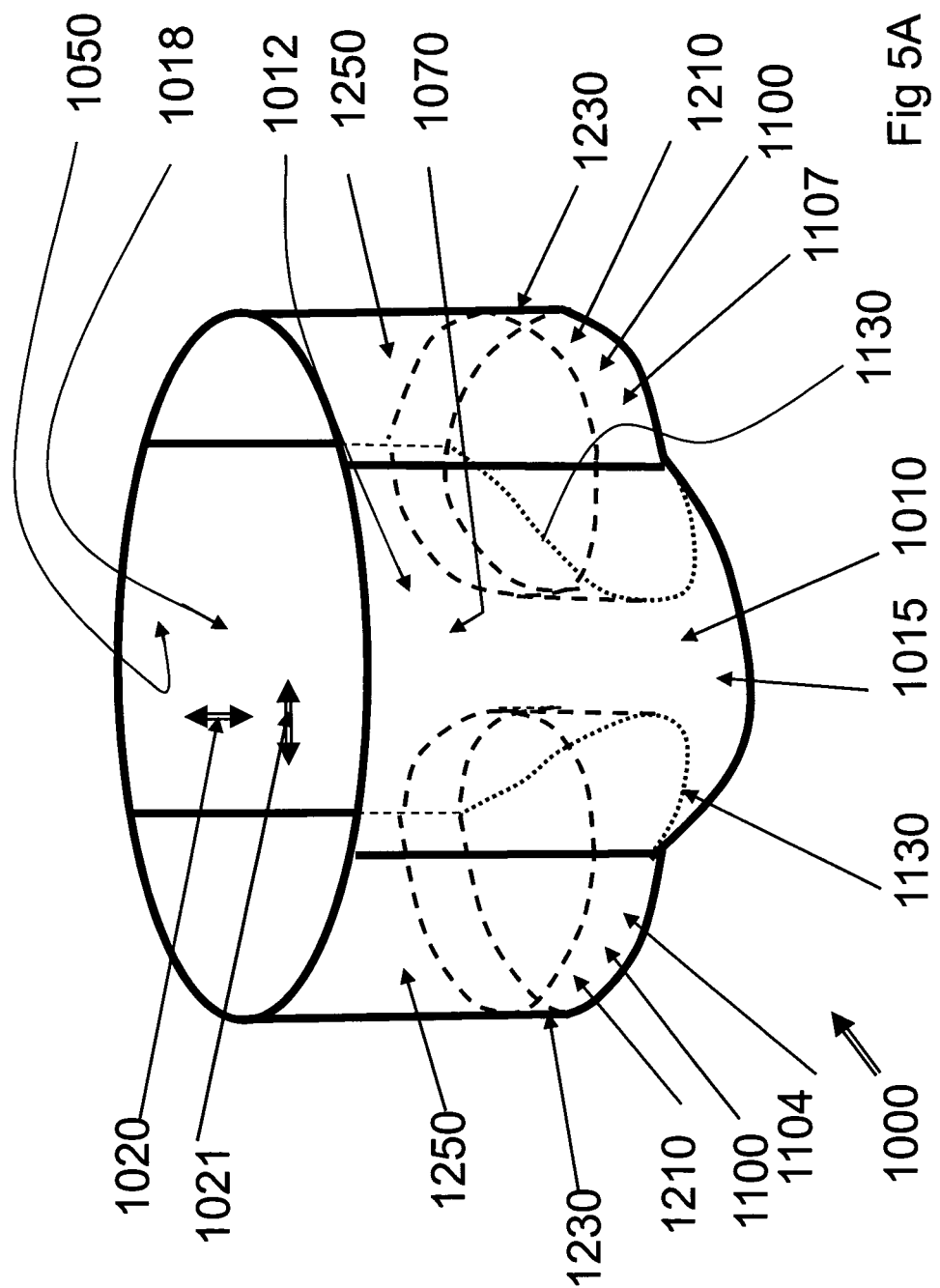

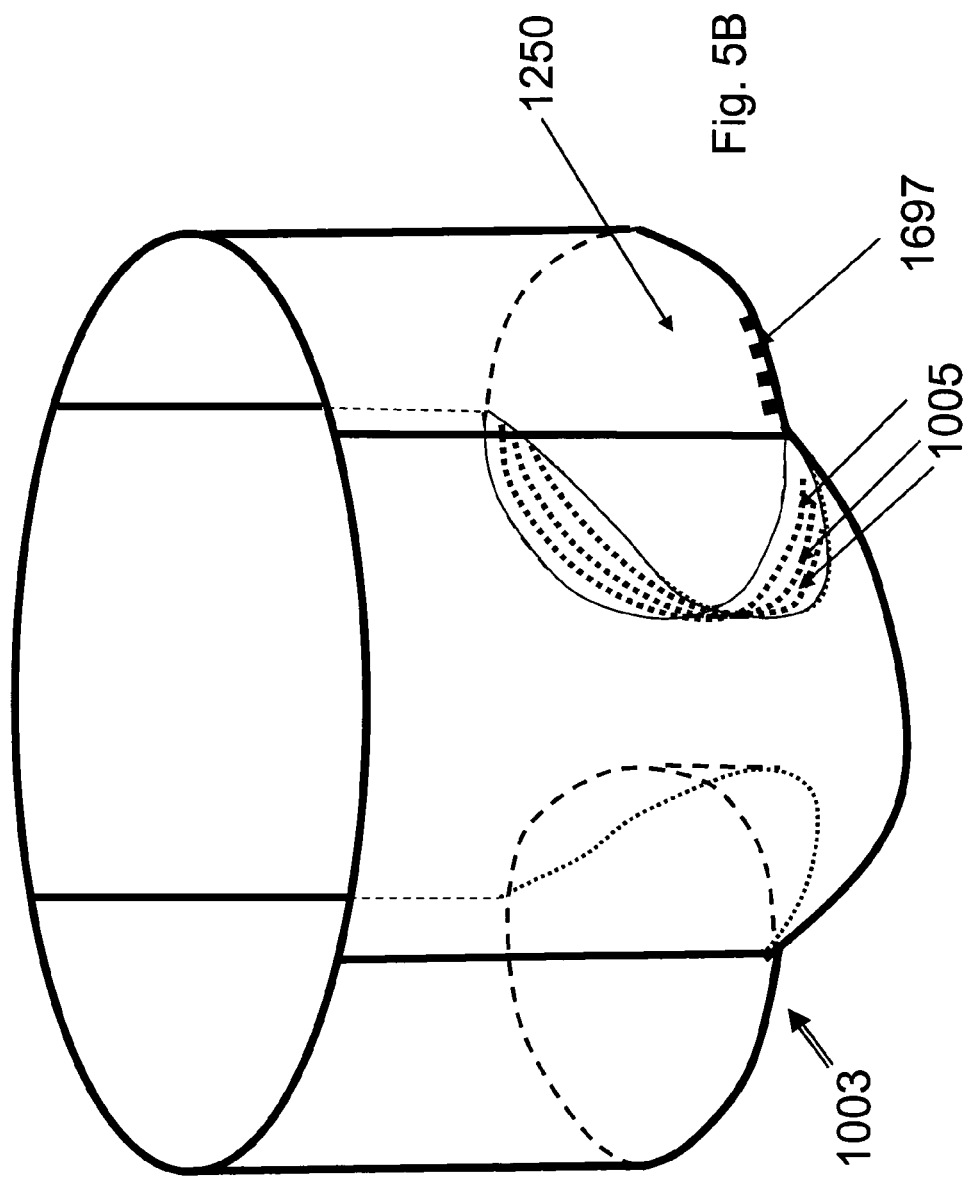

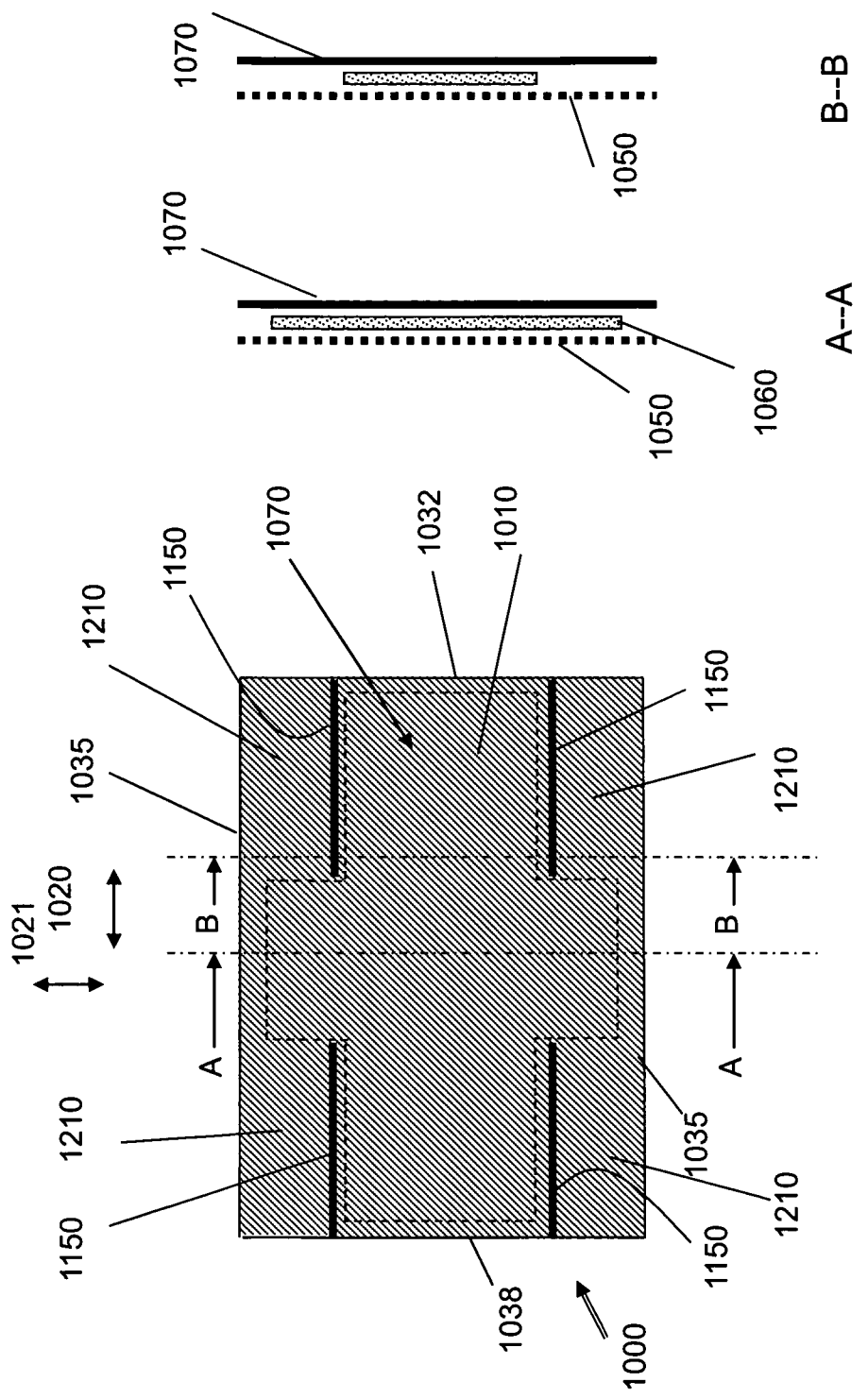

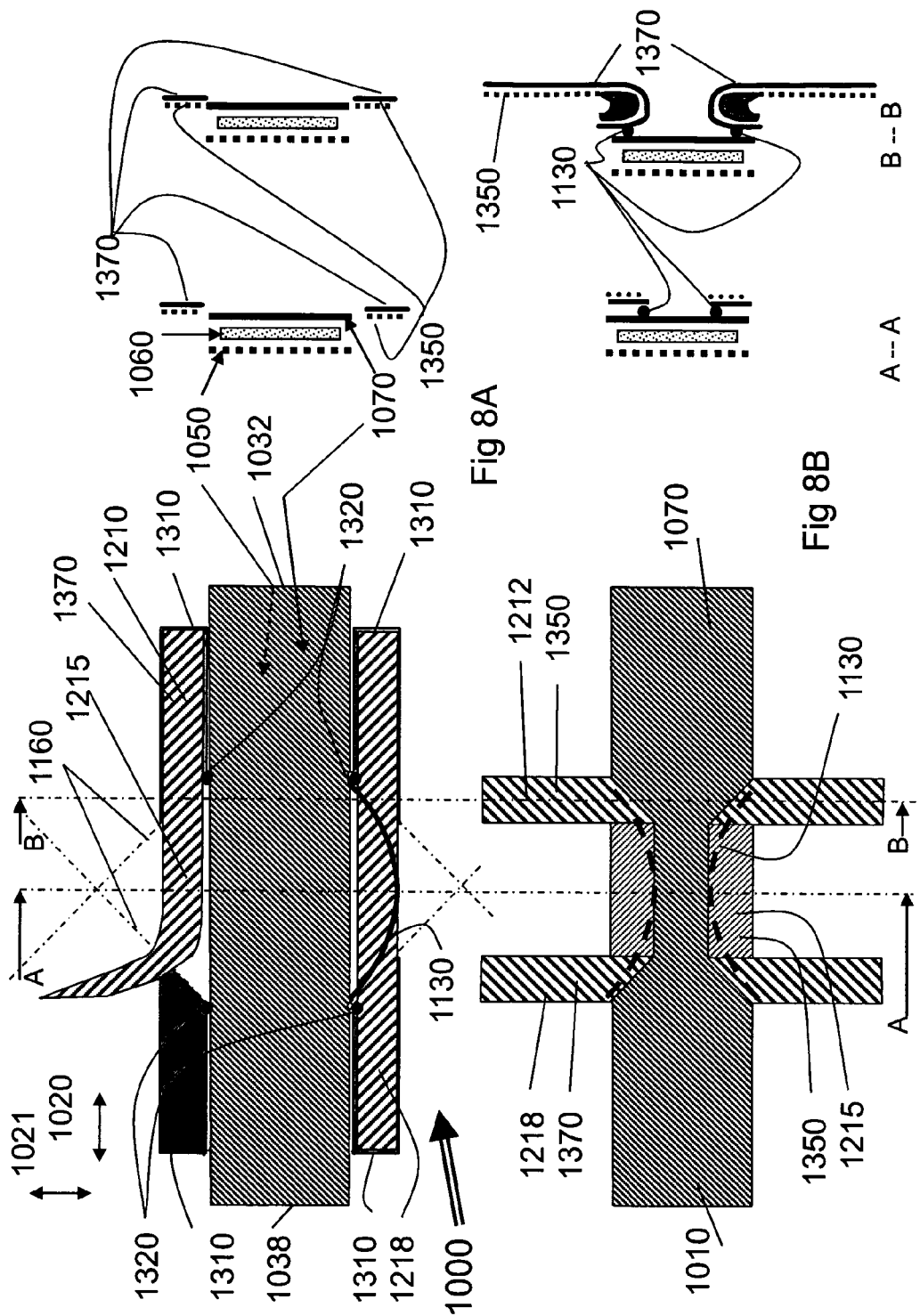

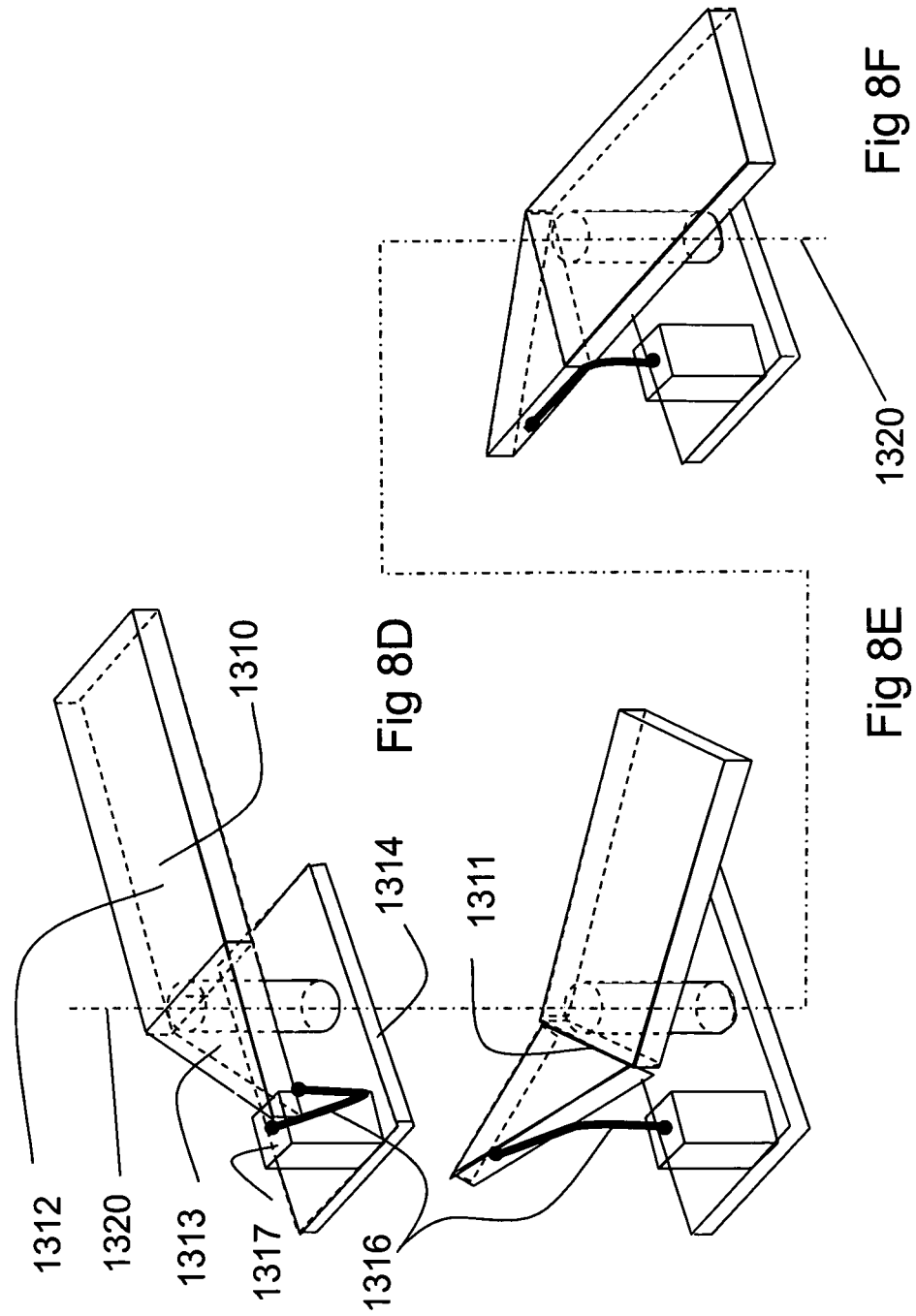

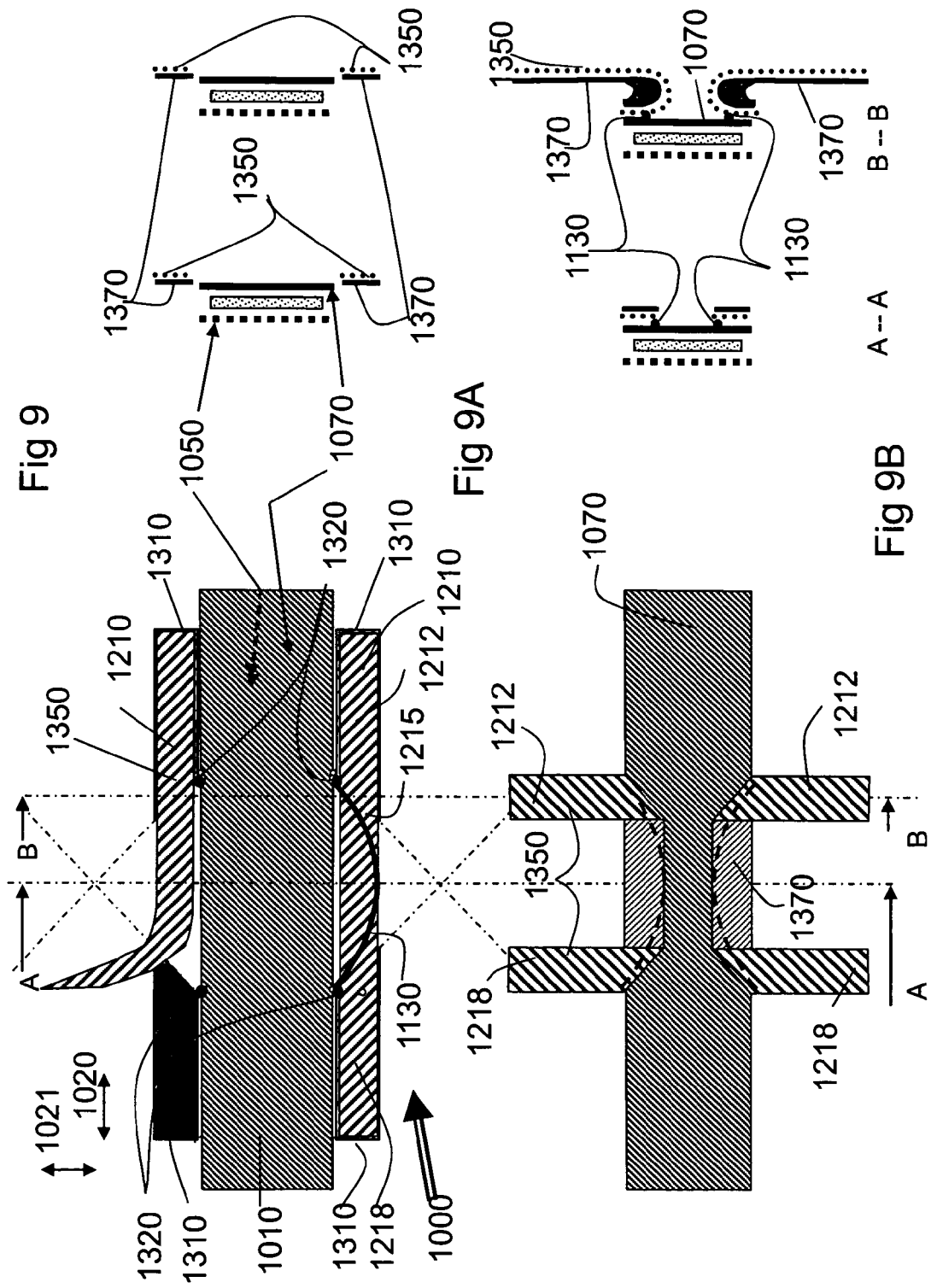

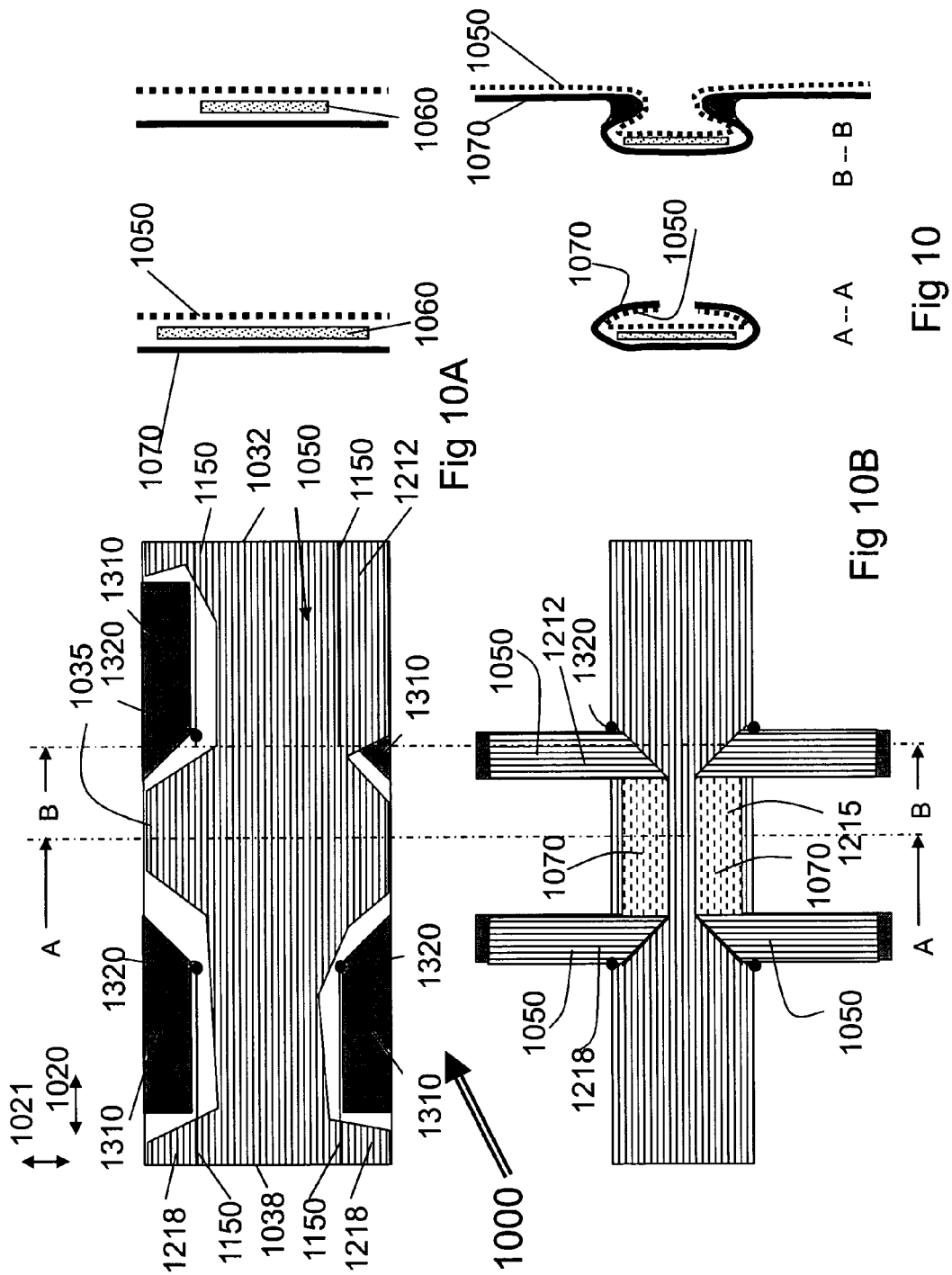

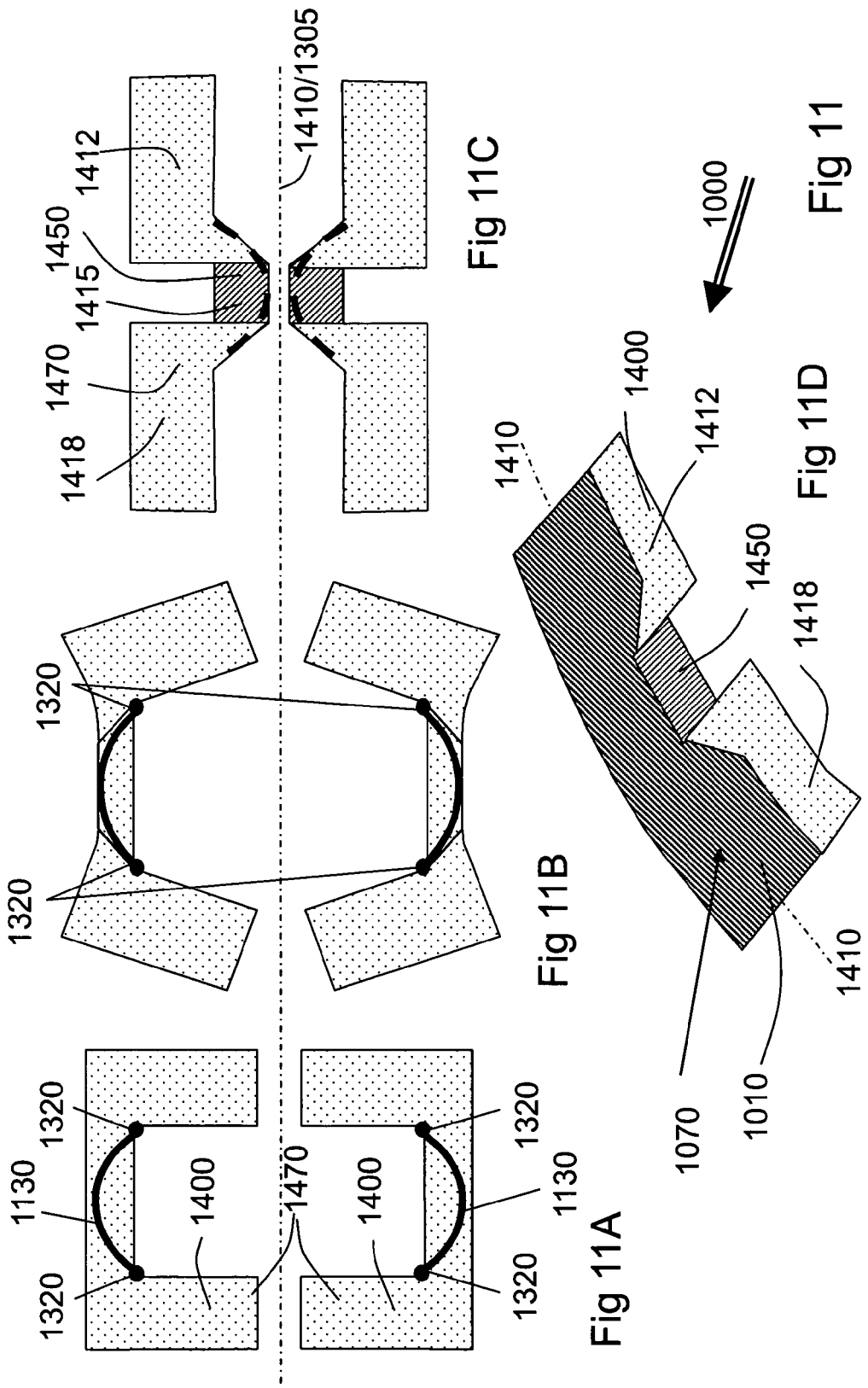

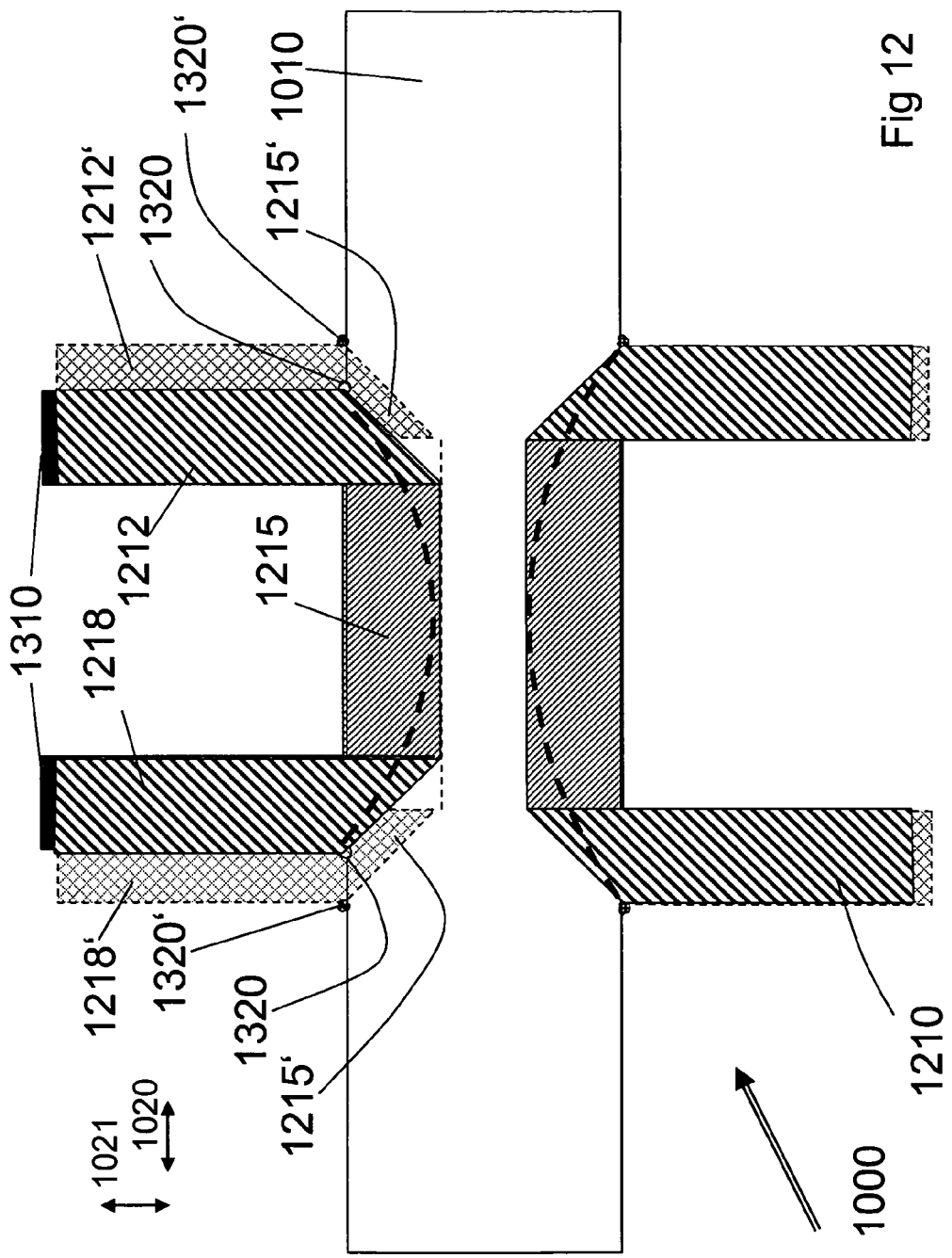

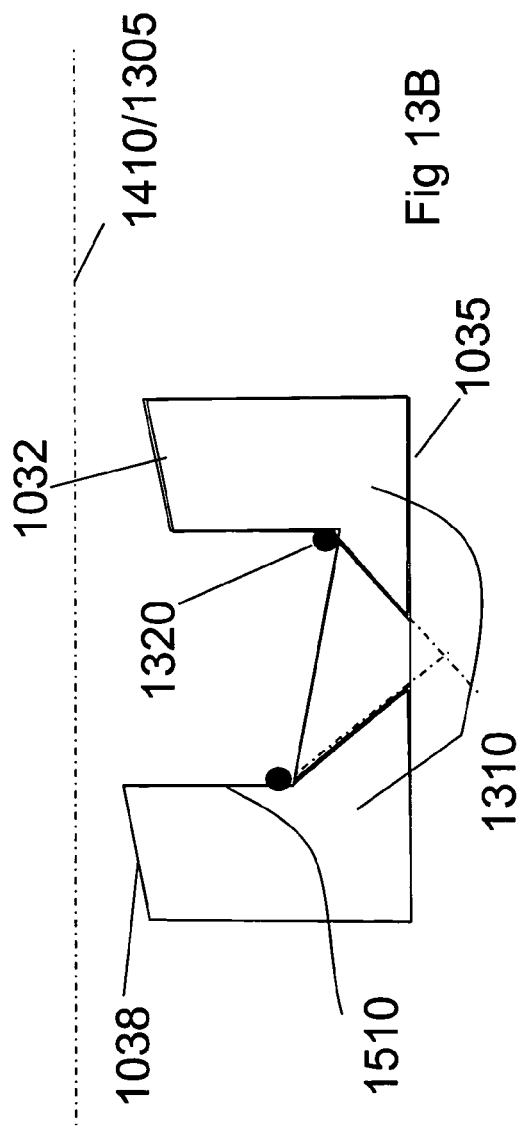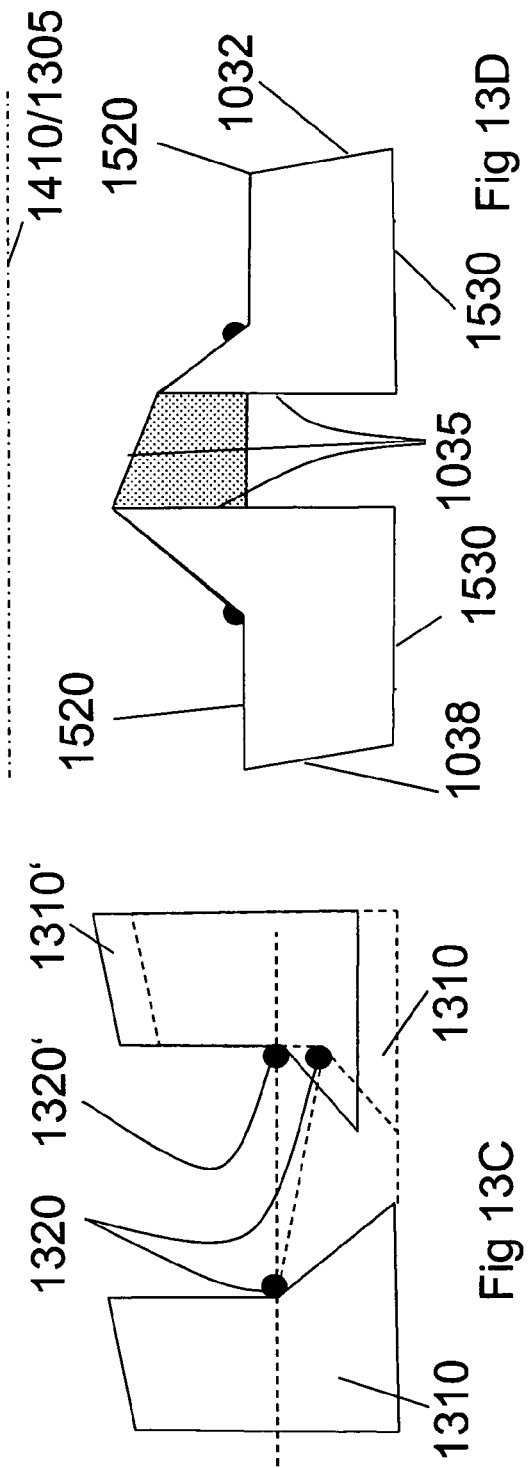

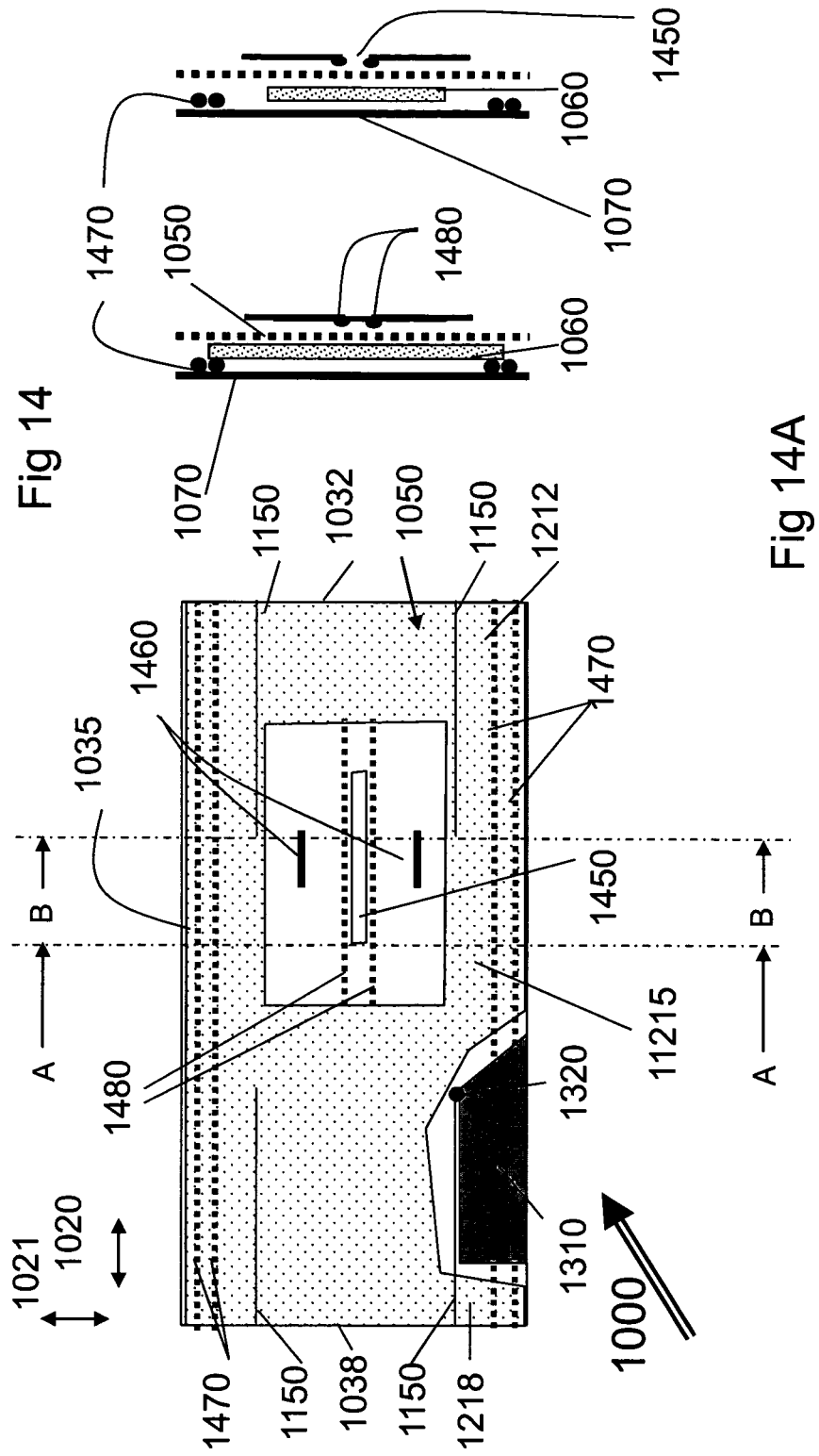

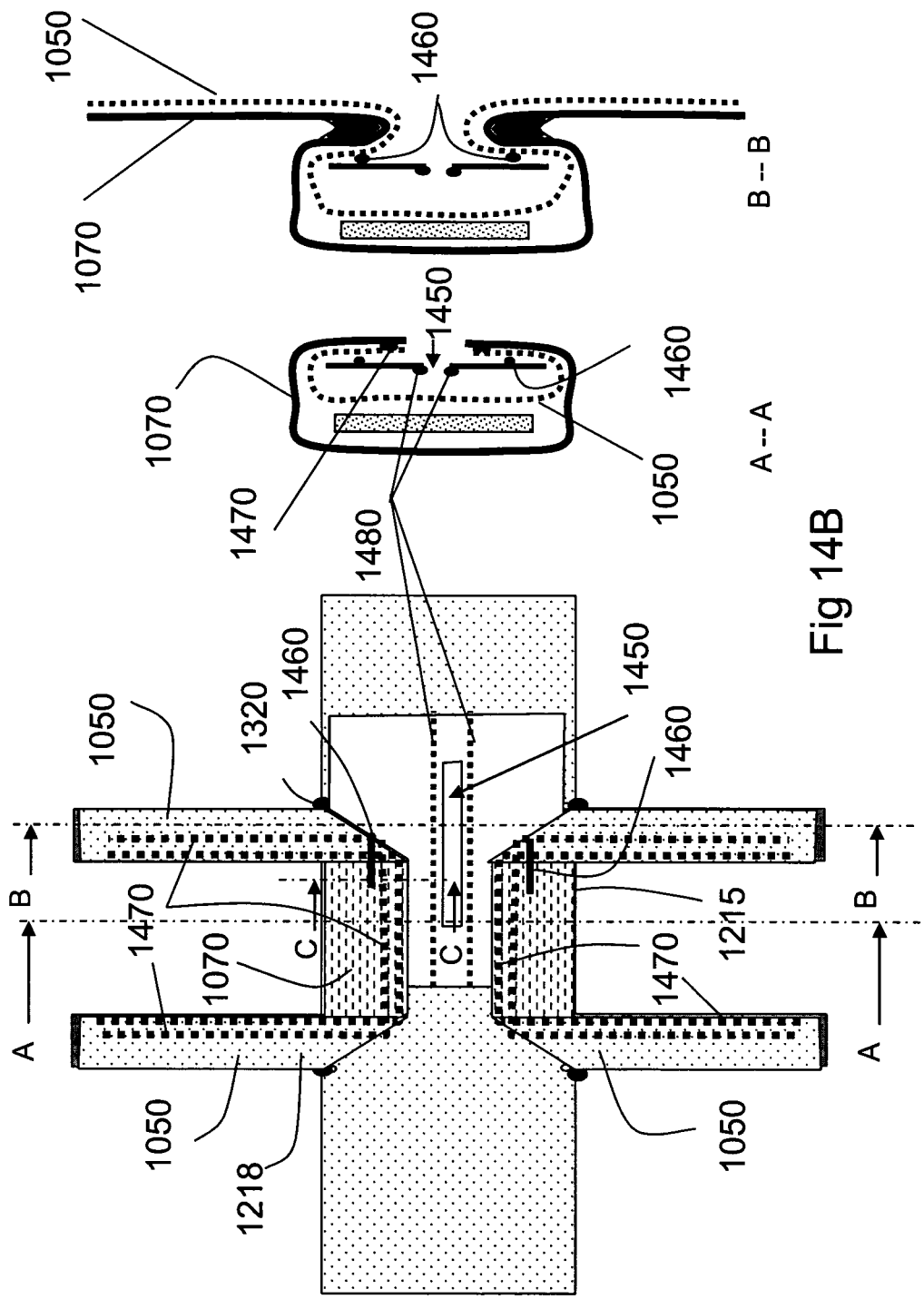

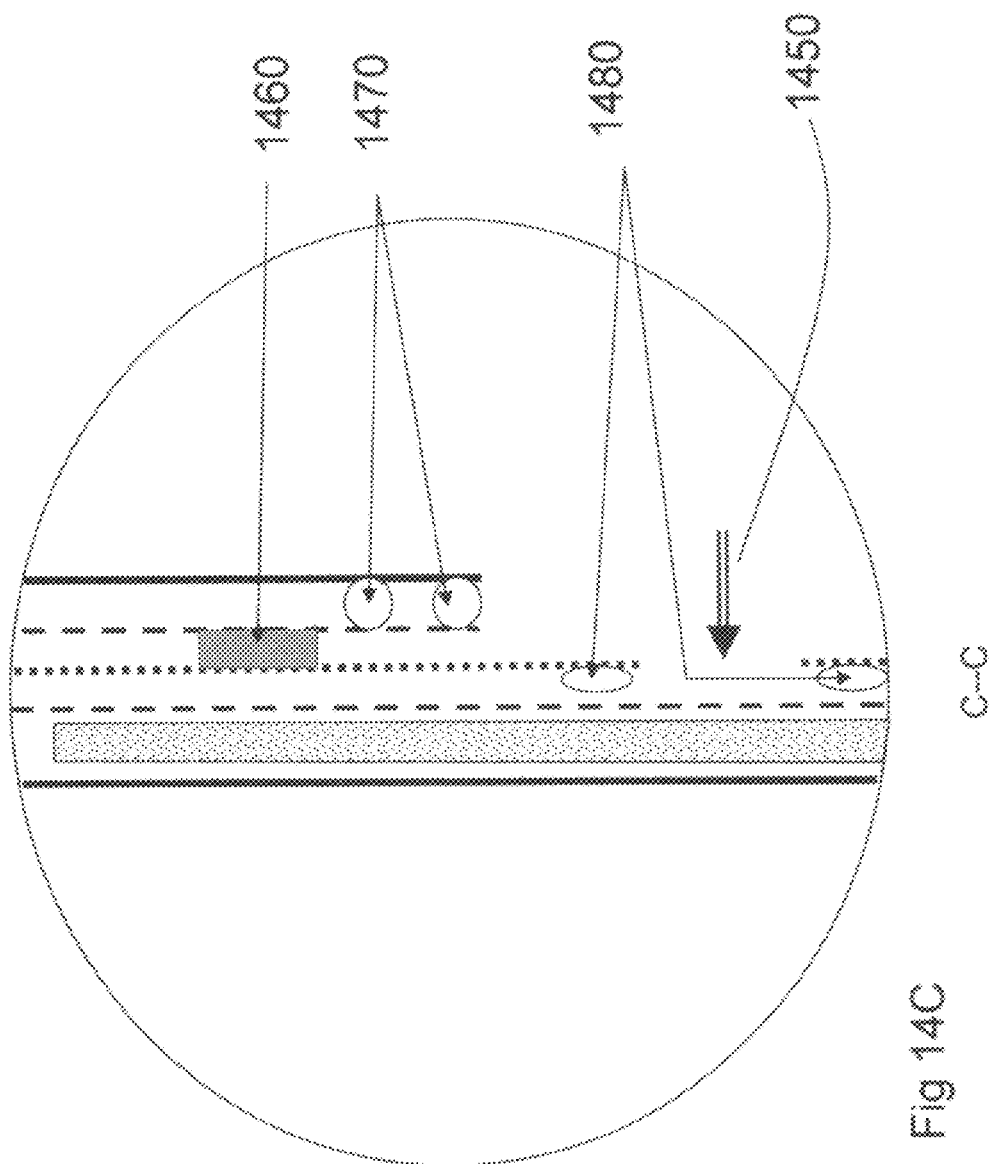

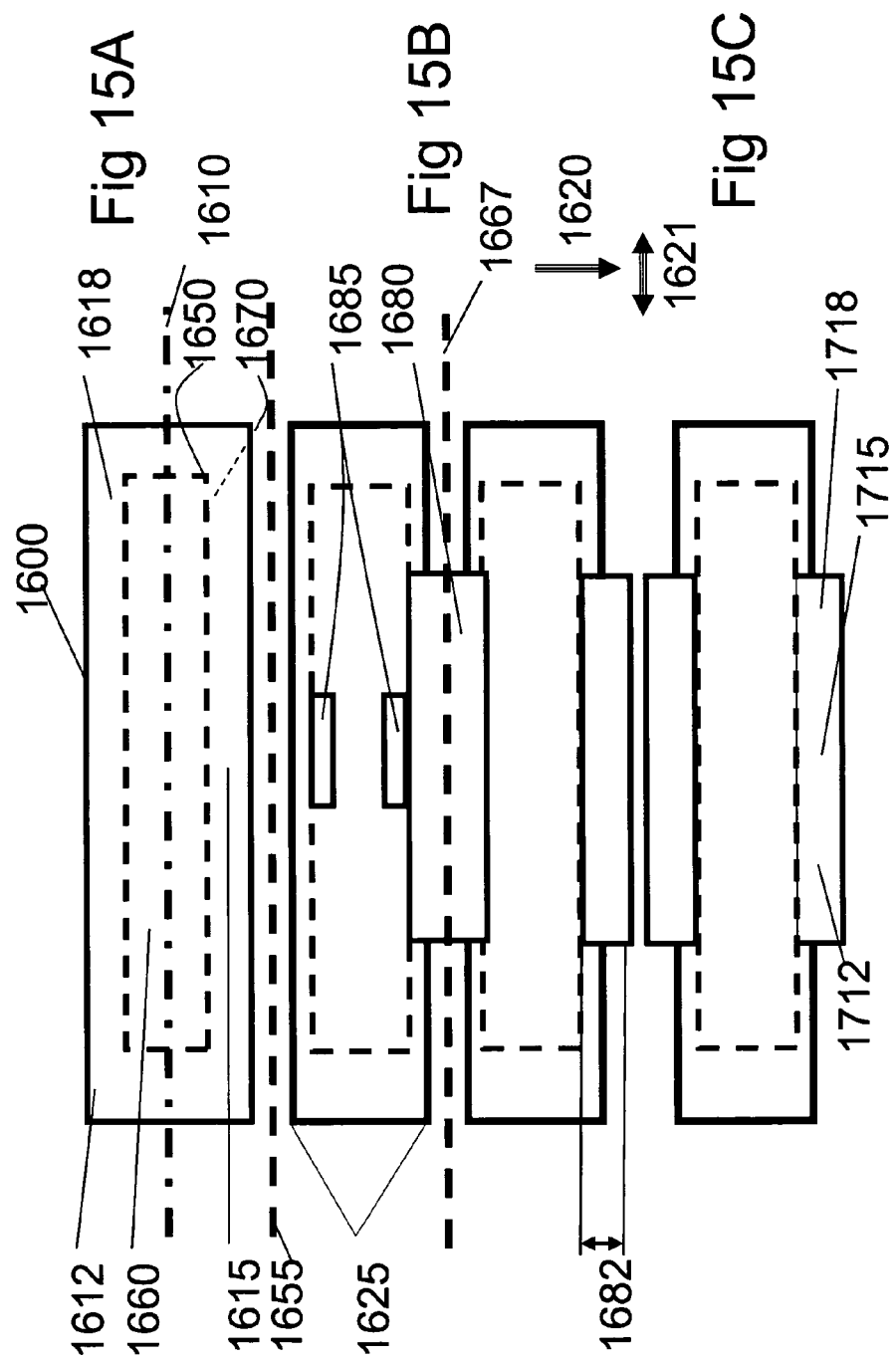

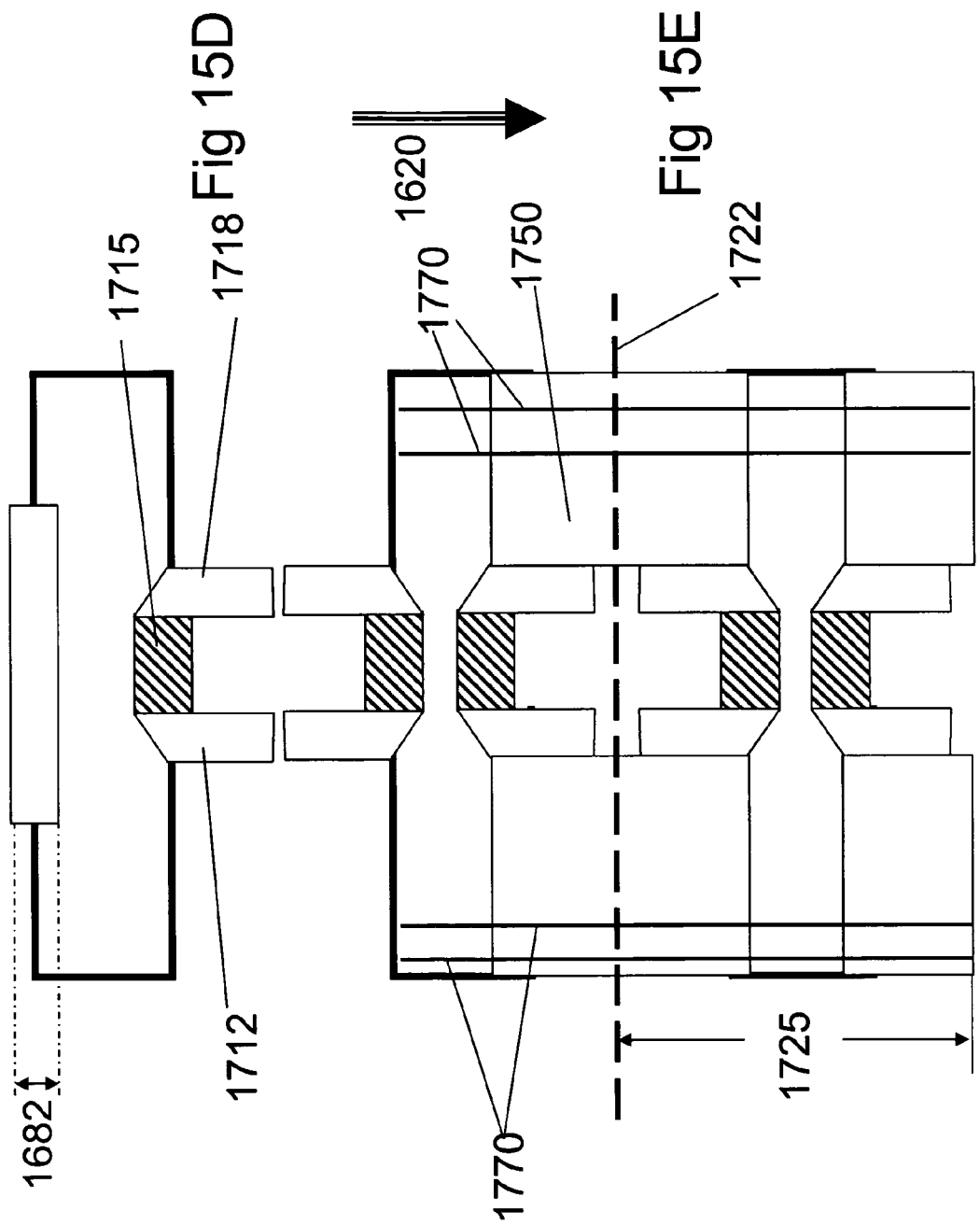

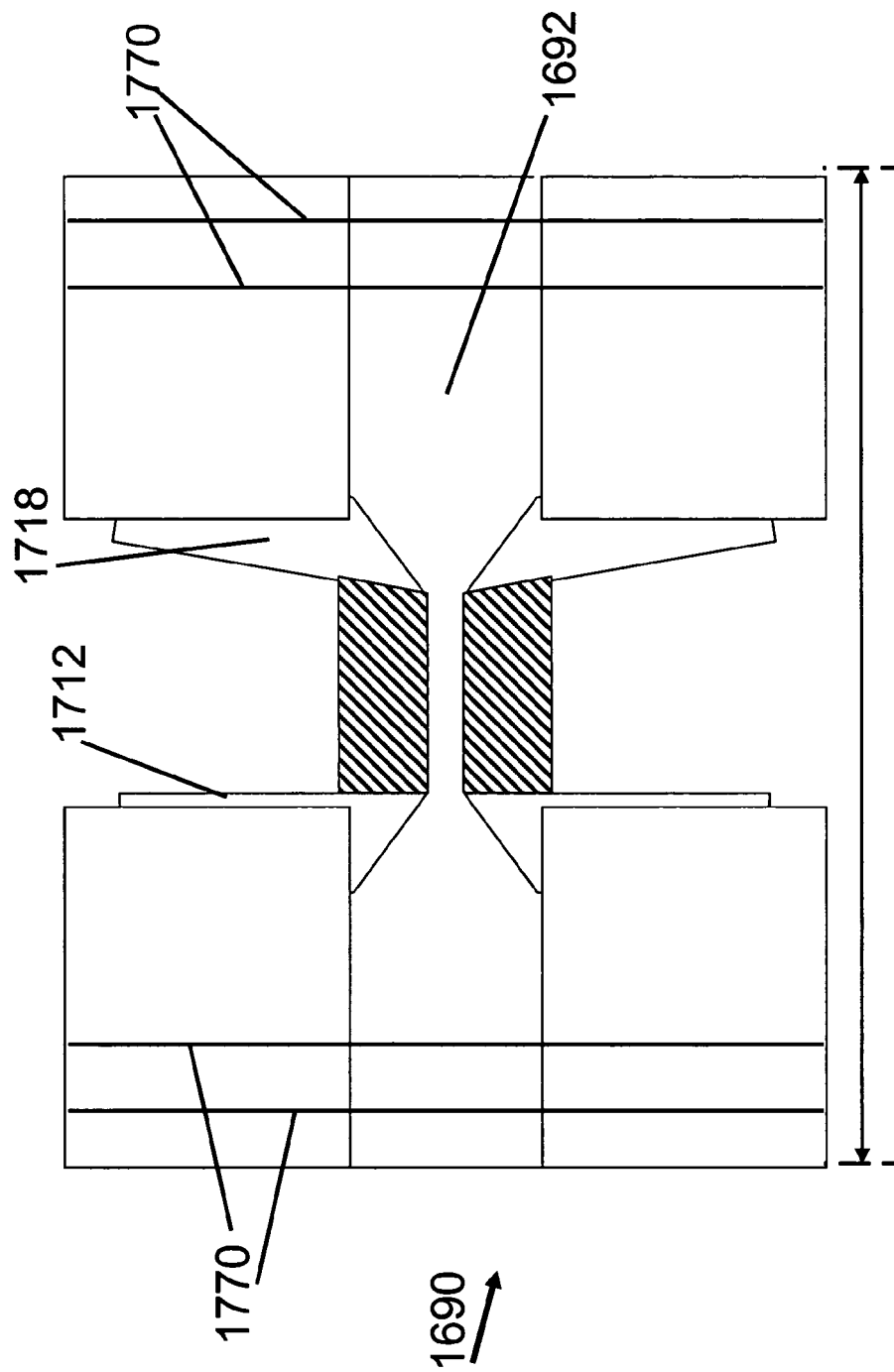

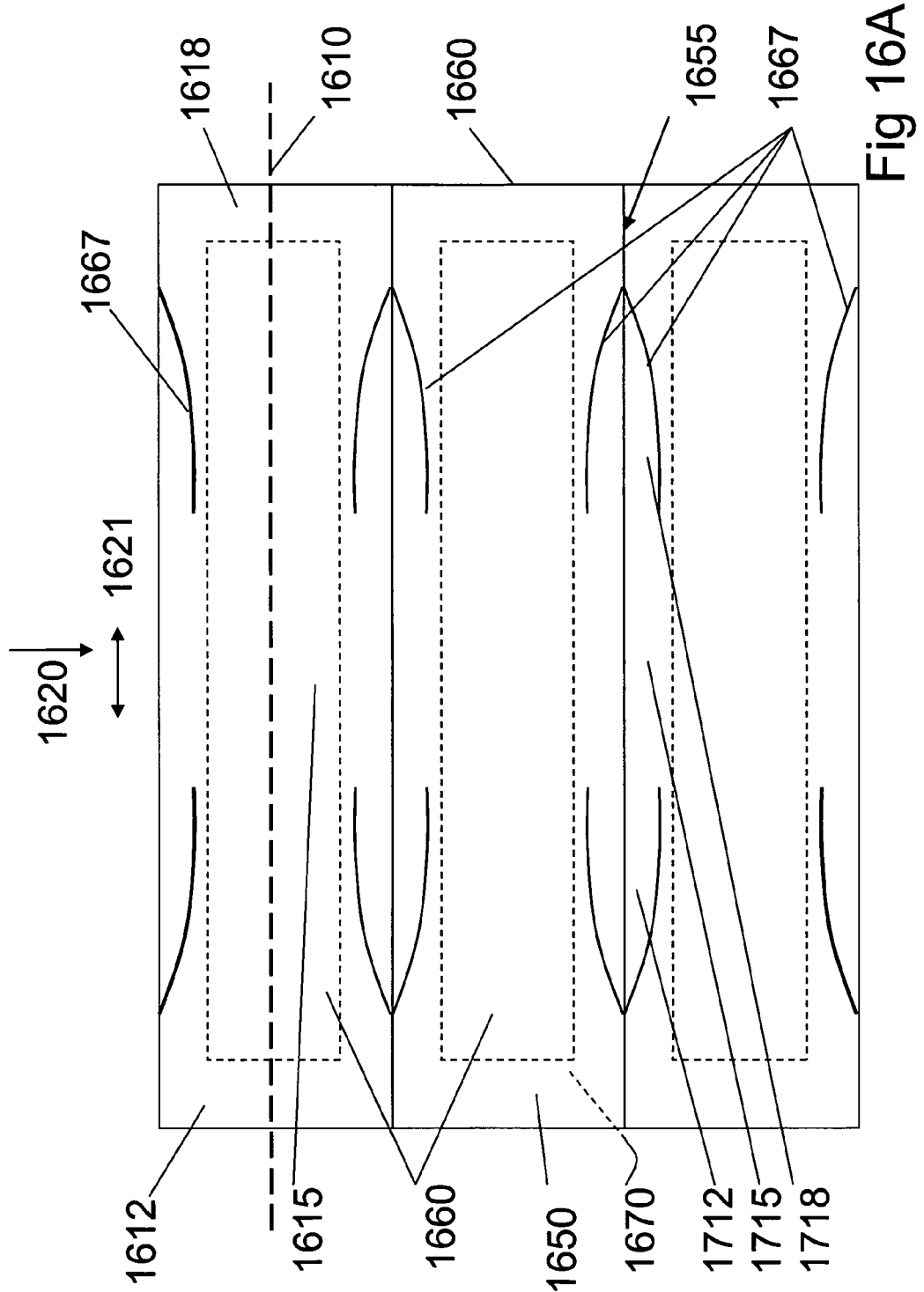

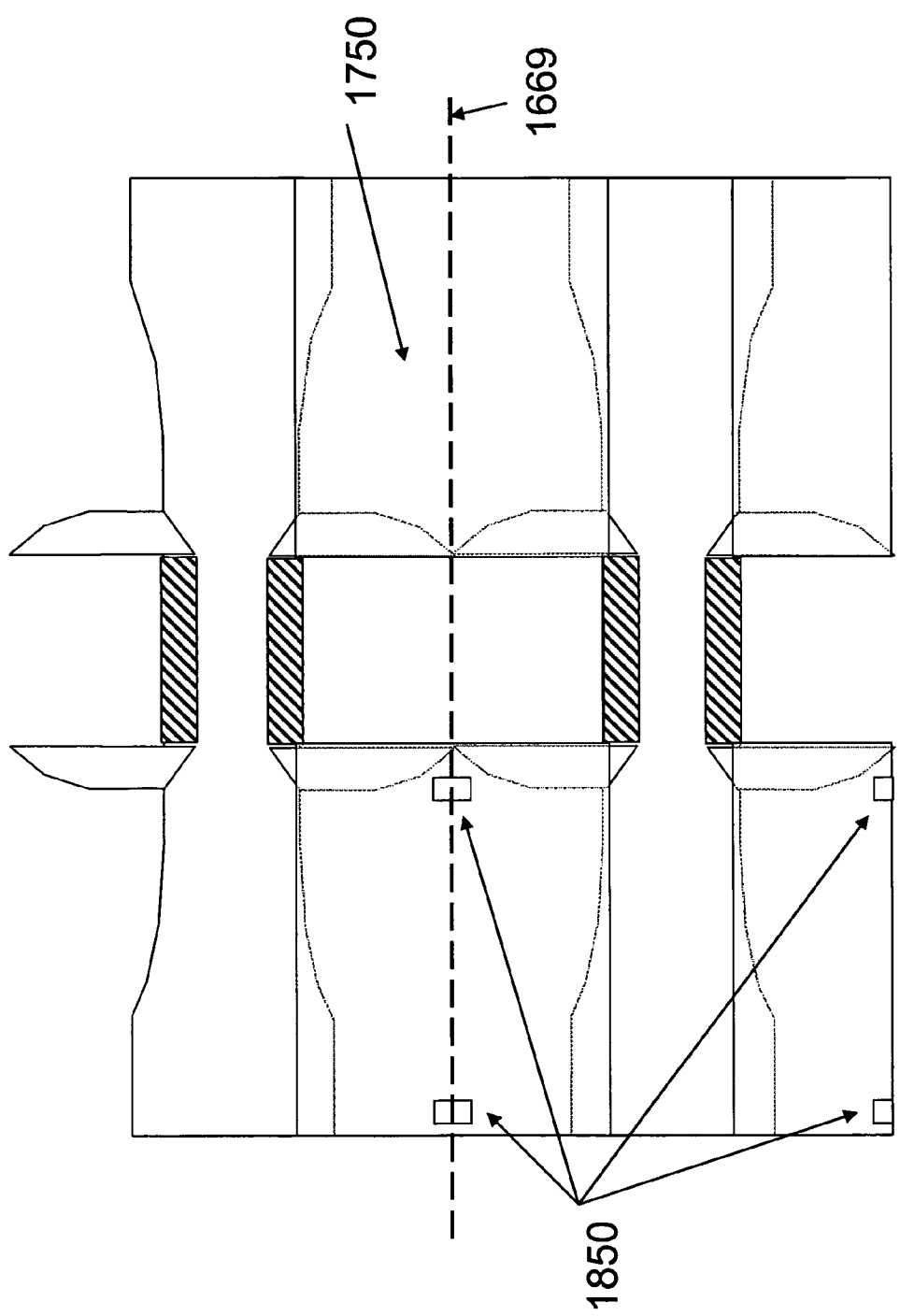

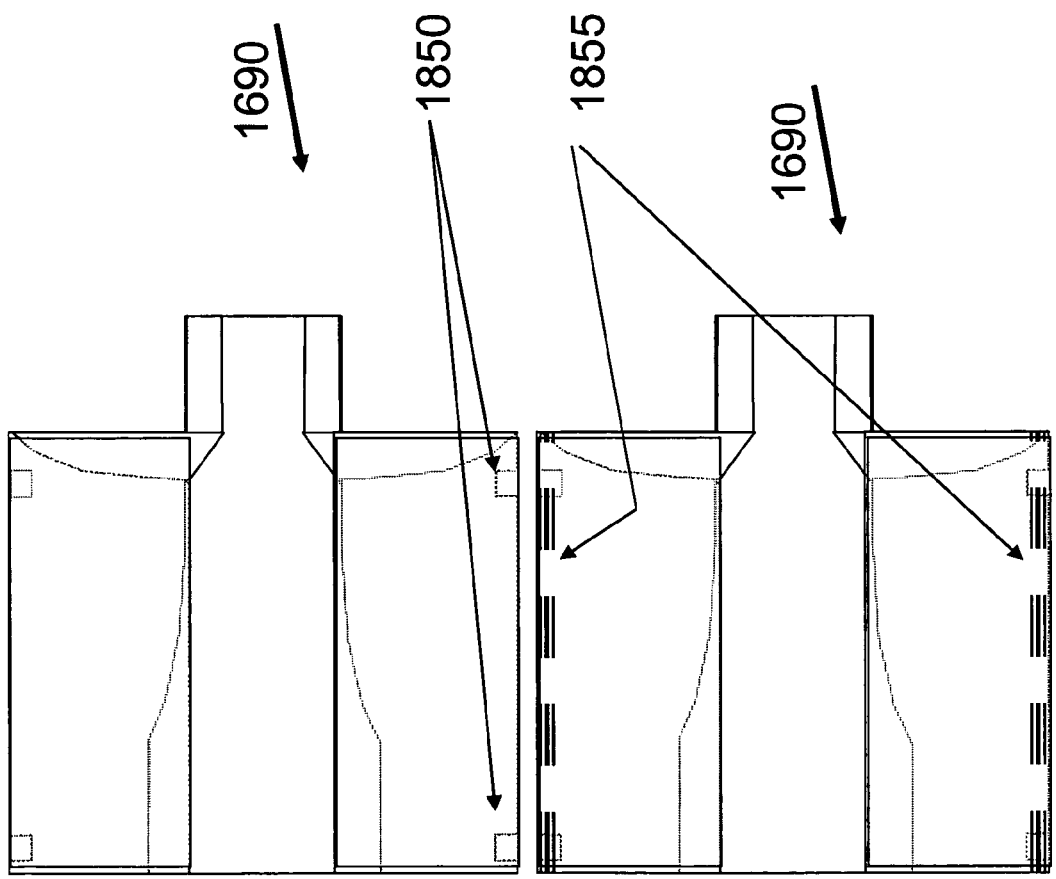

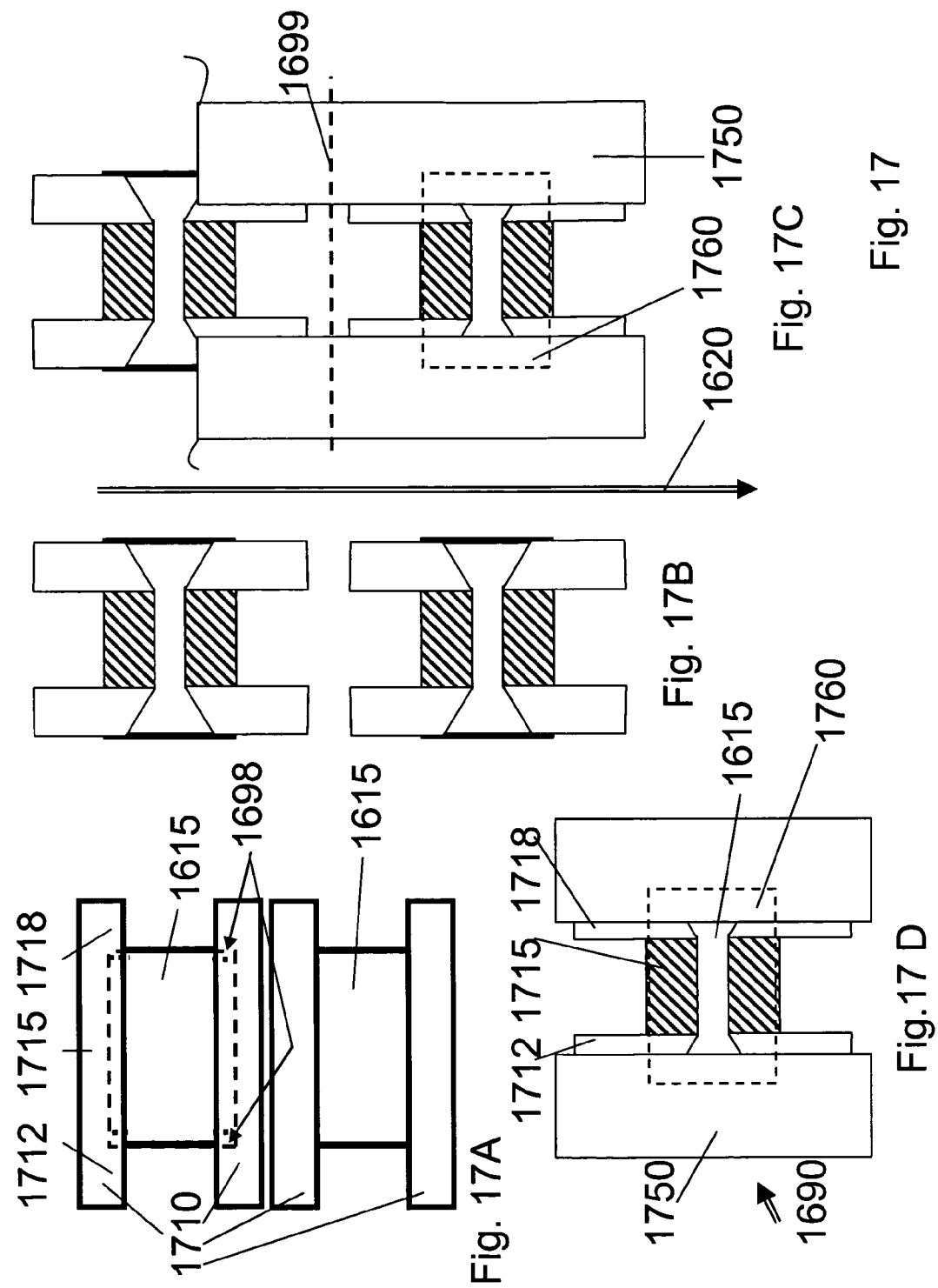

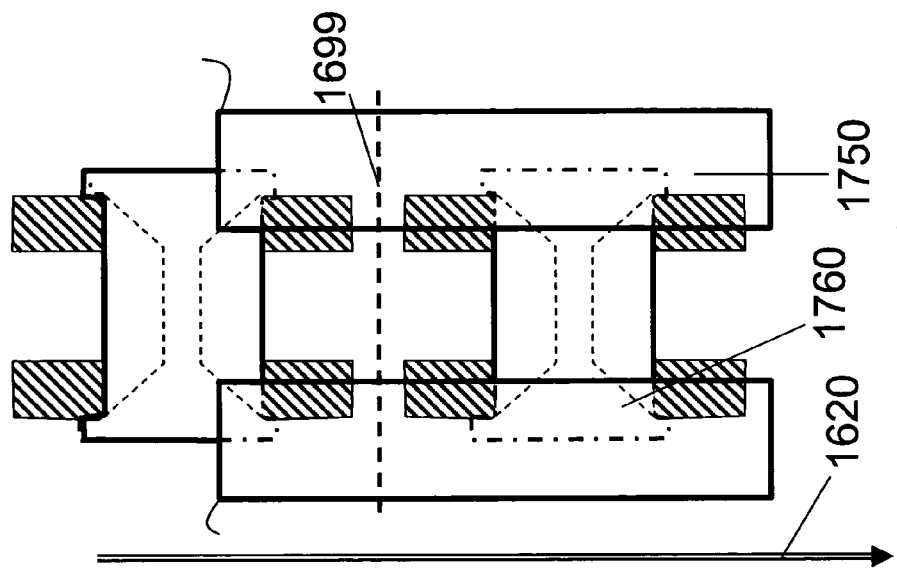
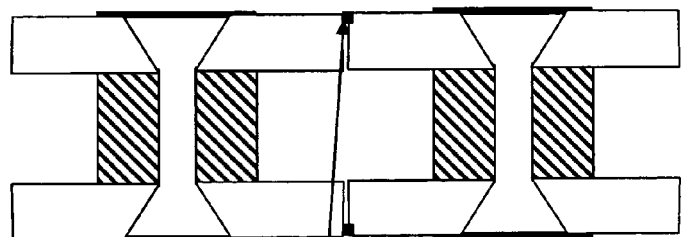
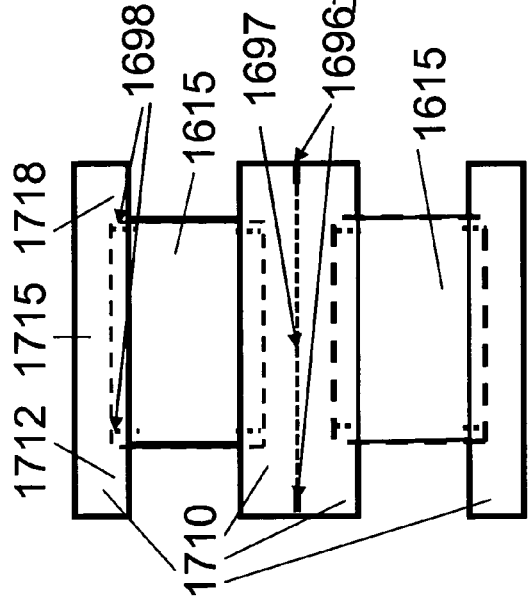
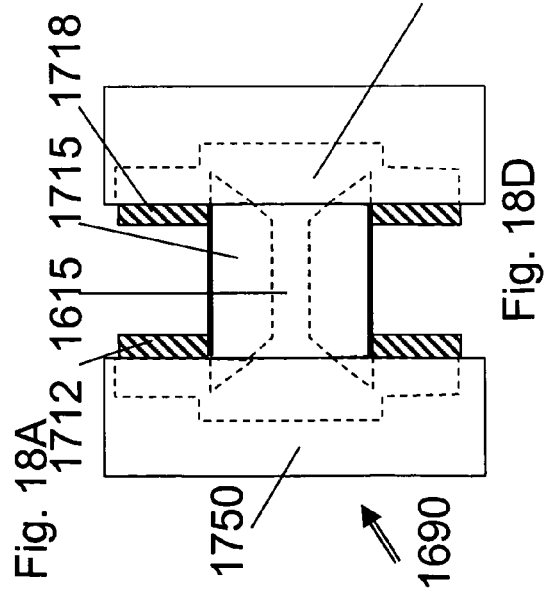
Fig. 18

MANUFACTURING METHOD FOR THE MAKING OF ARTICLES OR PRECURSORS COMPRISING HOOPS

CROSS. REFERENCE TO RELATED APPLICATIONS

This application is a U.S. national phase application under 35 U.S.C. §37 based upon co-pending International Application No. PCT EP2009/005814. Additionally, this U.S. national phase application claims the benefit of priority of co-pending International Application No. PCT/EP2009/005814 filed on Nov. 18, 2009. The entire disclosure of the prior application is incorporated herein by reference. The international application was published on May 27, 2010 under Publication Number WO 2010/057543 A1.

FIELD OF THE INVENTION

The present invention is a process for forming pairs of pre-forms for hoops for being used in articles or precursors of such articles comprising such hoops, such as pants or a pants-like structures, such as baby or incontinence diapers, absorbent pants such as training, feminine hygiene or adult incontinent pants, or garments like underwear, such as reusable or single use pants, all exhibiting particularly good body conforming fit.

BACKGROUND

Conventional processes of manufacturing belts suitable for clothing, garments, or apparel are typically done by very slow production processes, including sewing which cannot be done on high-speed machines. It is conventional in the garment industry, to make belt loops by folding a long strip of fabric longitudinally, usually the same fabric as used for the rest of the garment. The seam may be closed by stitching with a specialized seaming machine to form long continuous webs, or by gluing, or thermo-bonding, or by other conventional means. These webs are then fed into a second specialized machine designed to cut the webs into relatively short strips of suitable lengths for subsequent sewing of the garment in the form of belt loops. In U.S. Pat. No. 4,975,140, it is described to cut and seal such strips simultaneously.

U.S. Pat. No. 6,681,406 (Timberland) relates to the making of garment belts including an extendible insert, which may flex or stretch, while the belt is being worn so that the belt adapts to variations in the wearer's waist size and shape.

U.S. Pat. No. 4,134,154 describes the making of a belt preferably of a polyethylene material, where the cutting edge as well as side walls and holes are fused by the application of heat thereto to avoid the unravelling of the thermoplastic material. The longitudinal closing is performed by sewing.

However none of the disclosed processes allows the manufacturing of belts at very high production speeds, in particular, if these belts are composed of several materials or pieces. In the present context, very high production speeds relates to the manufacturing of more than about 500 items of Baby products, or 300 items of adult incontinence products per minute, corresponding to manufacturing web speed of more than about 250 m/min. Such mass production is typically based on web materials such as but not limited to the ones described in the above mentioned U.S. Pat. No. 4,134,154, namely synthetic materials, although conventional belt materials such as leather or woven materials may be used.

A particular application of a belt or a hoop structure is in articles or garments, which are worn on the wearer, mostly though not exclusively on a human wearer. Therein, hoops may encircle the waist of a wearer, such as conventional belts do. They may also encircle the head, legs or other extremities of a wearer, such as headbands or sock suspender do. Other articles may include both a waist hoop and leg hoops, as pants may do.

The manufacturing of pants-like structures is well known in the art, often described for disposable diapers or pants. Also here, high speed production refers to production speeds in the order of magnitude of 500 to 1000 articles per minute, corresponding to even more than about 500 in/min. Out of the plethora of publications, reference is made to EP1428487A1, EP1224875A1 or U.S. Pat. No. 6,098,557, describing the long followed approach of adding various elements to a continuous web, cutting this composite web into articles shortly before packaging, just followed by folding and optionally by closing the folded articles to form pants or pants-like structures. The webs, chassis elements, and articles remain essentially flat throughout the manufacturing, whereby the partly or fully assembled article may be flat folded onto other parts. Also in U.S. Pat. No. 6,926,702 an essentially 2-dimensional diaper is disclosed, where leg extensions are connected to the crotch region.

In contrast to such conventional approaches, a more recent approach has been developed by Concepts for success e.K. (C-4-S) and published in various patent publications (WO 06/102974A1, WO 08/037281A1, WO 06/103487A1, or WO 061102973A1 filed as PCT application PCT/EP2008/003844, unpublished—hereinafter referred to as the PCT'3844 application), which altogether are hereinafter referred to as "recent C-4-S applications". The articles as described therein can assume a particularly well fitting body conforming shape by having leg features, such as leg cuffs or leg hoops, which are connected to the centre region of the article along a curved connecting line. Upon donning of the article these leg features are up- or downwardly folded, such that they neatly conform to the shape of the legs of the wearer, thereby achieving good sealing against leakage whilst being very skin friendly. Further the articles can assume a 3-D shape, preferably in the form of a concave cup shape, so as to readily receive bodily discharges.

The recent applications also disclose manufacturing processes and corresponding equipment arrangements for producing such articles.

In the PCT'3844 application articles such as pants or pants-like structures are described, which comprise leg hoops which are folded over along a fold line and which encircle the legs of a wearer during use, and to the manufacturing of such articles. The leg hoops are manufactured by flipping front and rear parts of the hoop material, thereby creating the hoop structure which is essentially with one and the same surface in contact with the skin of the wearer. For certain designs as described therein, the body conforming 3D or cup shape of the article is further supported if the leg hoop is folded upwardly (i.e. the lateral edges in the crotch region are oriented towards the crotch crease of the wearer during use).

Whilst the methods as described therein are very flexible for most product design applications, they pose certain limitations such as to the relative positioning of certain article features. Henceforth, it is an object of the present invention to provide an alternative process for forming articles, and also to provide certain specific article designs.

SUMMARY

The present invention relates to a method for forming a-pre-forms for pairs of hoops on a high speed production line from web material(s) for the manufacturing of an article to be worn on the lower torso of a wearer or precursors therefore. The hoops are connected to a centre piece web material and comprise a centre hoop region and a first and a second extension region. The centre piece web material is adapted to be positioned in the crotch region of a wearer during use by comprising a crotch region exhibiting a front and a rear margin and side margins, thereby defining a longitudinal in-use orientation of the article/pre-cursor along a longitudinal article centre line during its intended use on a wearer. It may optionally comprise a front and/or a rear region extending beyond the front and rear margins of the crotch region so as to extend towards the front and rear waist region of a wearer during use.

The hoop and centre piece webs extend essentially in two dimensions with a thickness dimension (z-) perpendicular thereto and exhibit a first and a second opposite surface. The method comprises the steps of 1) providing the centre piece web material as an essentially continuous web material.
2) providing a hoop forming material. This hoop forming material may be provided as one or more (e.g. one for each side) essentially continuous web materials or cut pieces thereof or by separating the first and second hoop extension regions from a combined centrepiece and hoop material, which comprises the centre piece with the crotch region and front and rear extension regions, the centre hoop region, and the front and rear hoop extension regions. The centre hoop region extends laterally outwardly of the centre crotch region and the first and second hoop extension regions are separated from the front and rear extensions by hoop separation lines, optionally cut lines, sections of which extend predominantly along the longitudinal article centre line.
3) positioning or maintaining the positioning of the hoop web(s) such that the centre hoop regions are essentially in registry with the centre piece crotch region, each one with one of the side margins of the centre piece, and the front and rear hoop extension regions extend essentially parallel to the longitudinal article centre line forwardly and rearwardly of the centre hoop regions;
4) rotating each of the front and rear hoop extension regions around an z-directionally oriented axis such that the extensions are oriented outwardly and away at angles of between 45° and 135°, preferably 60° to 120° relative to the longitudinal article centre line and the hoop forming materials h are partly folded over themselves such that the centre hoop region is inverted and has an opposite surface orientation than the hoop extension regions.

Additionally, the method may further include the steps of
1) adding materials to form side panels preferably to form diapers, pants or pants like articles;
2) adding closure means so as to allow closure of the articles, preferably the diapers, pants or pants like articles;
3) adding elastification means;
4) adding a secondary topsheet materials;

In a particular embodiment, the hoop forming material is provided as one or more essentially continuous web materials or cut pieces, and wherein the rotating step 4) comprises the steps of
  i) affixing first and second extensions of the hoop material to support plates whilst leaving the centre hoop regions essentially unaffixed;
  ii) rotating the support plates around an essentially z-directionally oriented axis, such that the centre hoop region overlays the centre crotch region invertedly;
  iii) releasing the first and, second hoop extensions from the support plates;
  iv) optionally connecting the inverted centre hoop region to the centre crotch region.

The method of the present invention may be executed such that the longitudinal article centre line and the manufacturing equipment machine direction are essentially aligned/parallel.

Alternatively, the longitudinal article centre line and the manufacturing equipment machine direction are essentially perpendicularly arranged and wherein the method further comprises the process step 5) of increasing the spacing of two consecutive articles or precursors thereof along the MD direction of the manufacturing equipment. The hoop forming material can then be essentially separated from a combined centrepiece and hoop material, wherein the first and second hoop extensions are separated from the front and rear extensions by separation lines, optionally cut lines, at least sections of which extend predominantly along the longitudinal article centre line. Optionally the hoop material of a first and a second subsequent article or precursor remain partly connected during the step 5) of spacing apart the subsequent articles or precursor, and the first and second leg hoop extensions are rotated before, while or after the spacing step 5) is performed whilst the centre hoop regions are inverted by the rotating of the extensions.

BRIEF DESCRIPTION OF THE DRAWINGS

FIG. 3 shows a schematic view of a pants-like structure;
FIG. 4 shows a schematic view of a loincloth article;
FIG. 5 A shows a schematic perspective view of an article according to the recently published publications, and which may be manufactured according to the present invention;
FIG. 5 B shows a schematic perspective view of a conventional article;
FIG. 6 E shows a schematic view an article according to the recently published publications on a wearer;
FIG. 8 D-F show a particular embodiment of the equipment;
FIG. 9 to 11 show further articles at stages throughout their manufacturing processes according to the present invention;
FIG. 12 illustrates the stretching of the mid portion of the leg hoop material according to the present invention;
FIGS. 14 A and B (with corresponding cross-sectional enlargements B-AA; B-BB; and B-CC) illustrate an article according to the present invention comprising a secondary topsheet at stages throughout its manufacturing process.
FIG. 15 A-F show schematically the process steps according to the invention to form a hooped article.
FIG. 17 A-D shows schematically a further sequence of process steps according to the present invention.
FIG. 18 A to D shows schematically yet a further sequence of process steps according to the present invention.

Same numerals in the figures correspond to the same features.

DETAILED DESCRIPTION

The present invention relates to a method of manufacturing a pre-form of a hoop which suitably can be included in the manufacturing of a variety of articles comprising a hoop.

Such articles are typically worn by a wearer, such as a human wearer. Thus such articles may be garments or apparel, which may be worn directly on the skin of the wearer, or which may be worn over other articles. Such articles may cover a smaller or larger part of the body of the wearer Particular embodiments are articles which comprise a centre piece web material for connecting two hoops, such as in loincloth articles or diapers, pants or pants-like structures. Because of the easy manufacturing, such articles may be disposable, such as when being used as disposable underwear, or for operation theatre clothing. A particular application relates to pants or pants-like structures to be worn on the lower torso of a wearer, which comprise leg hoops, i.e. elements encircling the legs of a wearer during use, such as diapers, training pants, adult incontinence articles or other absorbent or non absorbent articles, which exhibit a particular good body-conforming fit.

Figure 1:
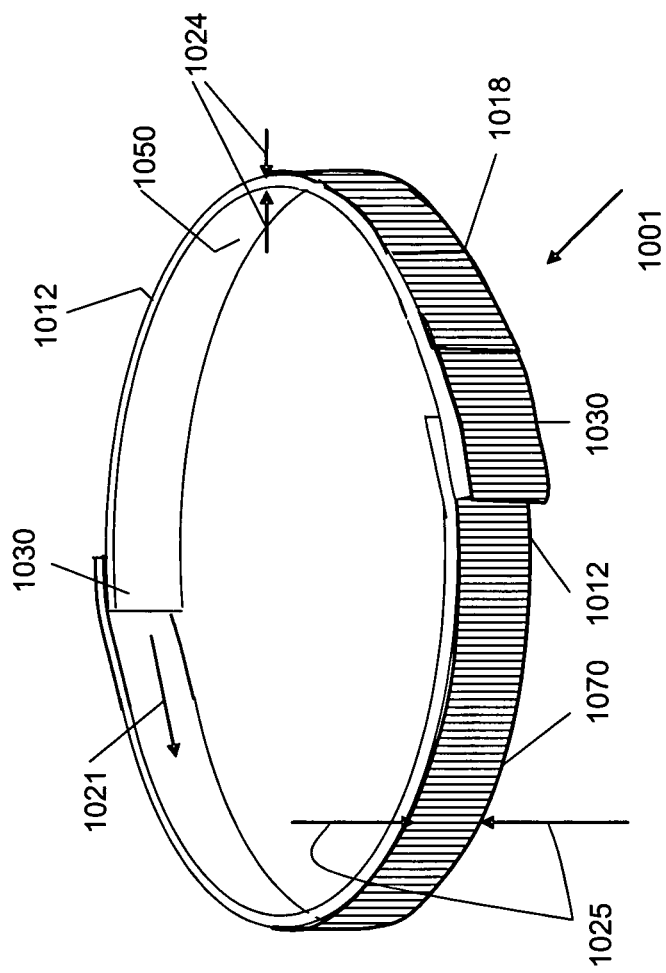
FIG. 1 shows a schematic view of a hoop structure.
Figures 2C, 2D:
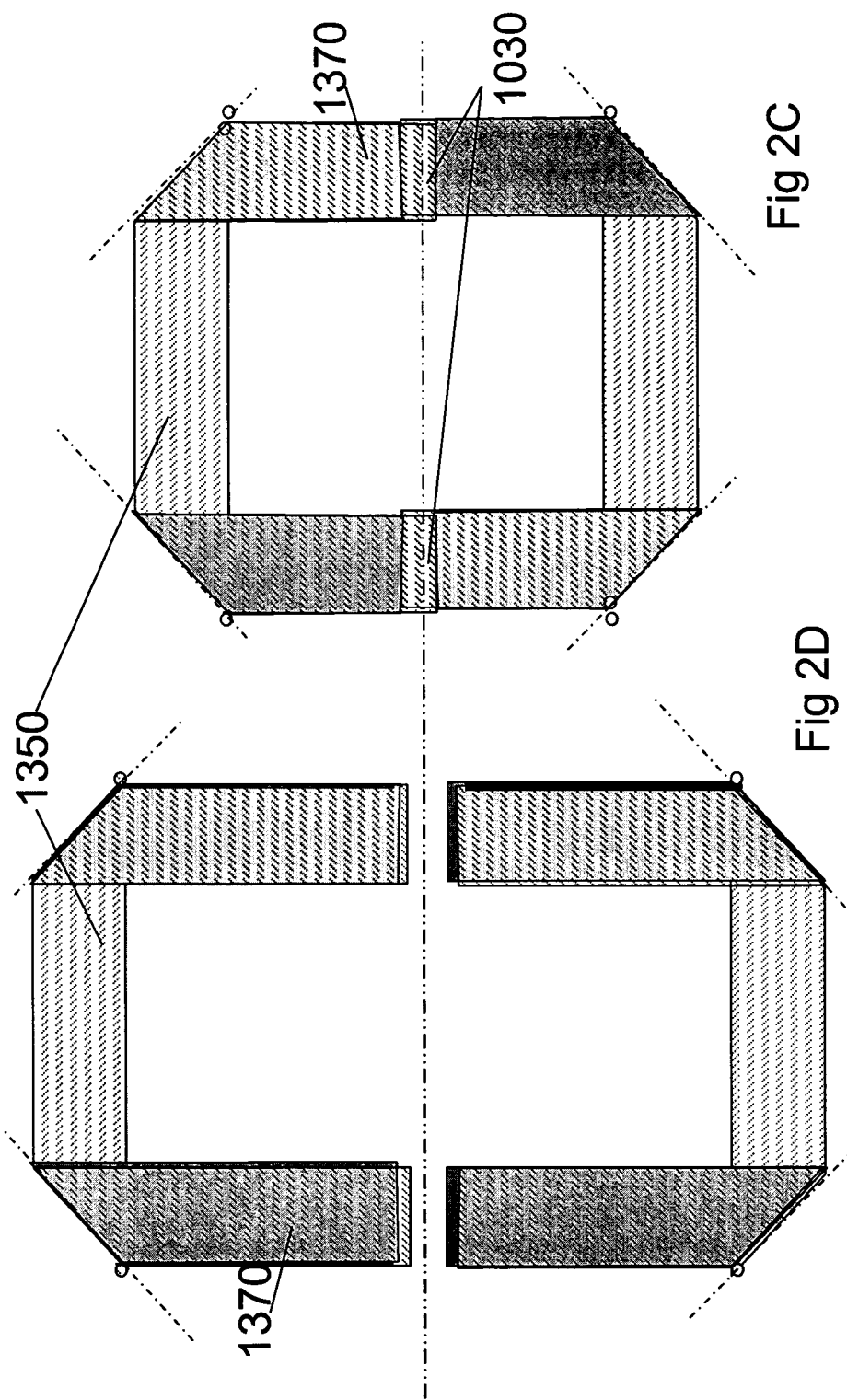
FIG. 2 shows a schematic view of the process steps for making a hoop or a pre-form therefor.

Within the current context, the term "hoop" refers to a circular strip of flexible material in particular in the context of a garment or apparel. Referring to FIG. 1, such a hoop 1001 forms a closed circular structure, which may, for example, be worn around the waist of a wearer (not shown). The hoop may have a hoop width dimension 1025 and a hoop thickness 1024. Perpendicularly thereto, the circumferential length (corresponding to the waist circumference of the wearer) may be measured along the length direction 1021 of the hoop. The hoop may have a wearer oriented surface 1050, and an opposite surface 1070. The hoop as shown in FIG. 1 has two connecting lines or regions 1030, here shown in an "overlap" design, which may connect the respective parts of the hoop permanently, such as by adhesive or thermal bonding, or releasably, such as by releasable adhesive tapes, or may be refastenable such as by using mechanical fasteners, such as of the well known hook-and-loop type. These connecting lines 1030 may be arranged so as to be positioned in the side regions of the wearer, such that one part of the hoop may be considered a front part 1012, and the complementing part the rear part 1018. The front and/or rear part may further be unitary, or may be made of separate pieces of material attached to each other to form the front or rear part. The hoop may be of a single layer or may be a composite material. The hoop materials 1210 may be a single or any combination as generally suitable for being worn as a garment or apparel, which typically can be described by exhibiting a certain strength, conformability, flexibility, suppleness, skin compatibility etc. In particular, the hoop material may be extensible (i.e. showing at least to a certain extension a relatively low resistance irrespective of retracting forces) or elastic (i.e. exhibiting at least within certain extensions certain retractive forces). During the manufacturing of a hoop, the hoop forming material may be arranged in a hoop pre-form. Within the present context, this refers to the arrangement of the hoop material such that a closed hoop may readily be formed. This is the case, when the ends of a belt forming material are already e.g. in an overlapping arrangement, and just need the connecting step to close the hoop. This may also be the case, when the parts of a hoop forming material are already repositioned and just need a conventional folding step to be in an arrangement allowing the closure of the hoop. A further way of forming a hoop may be to produce a pre-form, which by combination with another material may form the closed hoop. An exemplary way of making such hoops or pre-forms for a hoop is explained by referring to FIG. 2. Referring to FIG. 2A to 2D the forming of a hoop is explained, and in FIG. 2E to 2F the forming of a hoop pre-form. FIG. 2A shows the top view of a closed loop operating means 1300, such as described in more detail in the above referenced C-4-S applications. The closed loop operating means has a centreline 1305 along the machine (or x-) direction 1020, a width (or y-) direction along the cross machine direction 1021, and a manufacturing orientation 1304 along the machine direction (i.e. in the case of the closed loop operating means being a turret or a drum with a drum surface 1301, the drum rotates along a rotating axis parallel to the CD- or y-direction such that the surface moves along direction 1304, i.e. to the right in FIG. 2A). The closed loop operating means further has rotating equipment 1308 comprising support plates 1310, which are connected to the closed loop operating means via essentially z-directionally (i.e. perpendicularly to the upper x-, y-surface of the closed loop operating means) positioned rotating axes 1320. The rotating equipment 1308 comprises four rotatably mounted support plates 1310, each one positioned forwardly and rearwardly left and right (relative to the manufacturing direction 1304). As shown, each support plate 1310 is essentially shaped like an elongated trapeze, with a rectangular first section 1312, and a triangular second section 1313. This triangle is delimited by MD- and CD-lines as well as tapering line 1160, here shown at a 45° orientation. The rotating axis 1320 is positioned at the connecting line of the first and second sections, either inwardly of the trapeze (for outward rotation of the first section of the support plates as in FIG. 2E to 2F), or outwardly of the trapeze (for inward rotation of the first section of the support plates as in FIG. 2A to 2D). The support plates may be turned, for example by 90°, such that the first sections either rotate towards the centreline 1305 (hereinafter referred to as "turned inwardly") or away from centreline 1305 (hereinafter referred to as "turned outwardly") such that the second (triangular) sections rotate outwardly (when the first sections turn inwardly), or vice versa. The upper surface of the support plate (i.e. oriented away from the closed loop operating means) is adapted to receive web materials.

In order to manufacture a hoop as shown in FIG. 1, two strips of web material may be provided, which are selected by their properties to be suitable for the intended application. Typically, the hoop materials may be single- or multi-layer, bendable, supple, if appropriate soft to wearer's skin, optionally elasticated. Optionally, the hoop materials may comprise absorbent materials, and may expand when being wetted by body exudates such as urine or sweat, thereby capturing these and, such as when the hoop is used as sealing element, also tightening this seal e.g. towards the body. Being a web material, the z-directional extension is typically much smaller than the MD- and/or CD extension. The supply may be done by any conventional process, such as by providing a first and a second roll of web materials having the appropriate width and cutting strips having the appropriate length, or by providing one roll of web material, separating it into a first and second strip along a longitudinal line and along cross-directional lines. As shown in FIG. 2B, each one piece of the strip of web material 1210 having a mid or centre region and a first and a second extension region or portion extending forwardly and rearwardly respectively for forming the hoop is fed to the closed loop operating means, and positioned on and temporarily affixed to support plates on one side of the closed loop operating means, such that the leading portion of the strip

1212 is on a front support plate, and the rear portion 1218 is on the a rear support plate, whilst the mid portion 1215 is essentially unsupported there between. The web material is affixed with its first, downwardly oriented surface to the support plate, whilst the second, upwardly facing surface 1370 can be seen in FIG. 2B. The size and dimensions of the support plate may be essentially the same as the respective portion of the web material, or it may be slightly shorter such that the front or rear end of material 1210 extends beyond the edge of the support plate, or slightly longer (as shown in FIG. 2B).

Once the two strips of hoop web material 1210 are affixed to the support plates, the rotating mechanism is operated. In FIG. 2C, it can be seen, that after the rotation step, the first portions of the support plates have been rotated inwardly towards the centreline of the closed loop operating means. As the front (1212) and the rear (1218) portions of the hoop material remain affixed to the support plates, these will also turn inwardly, with their first upwardly oriented surfaces 1370 remaining upwardly oriented. The mid portion 1215 will inevitably buckle upward or downward and fold over itself (i.e. is inverted), such that now the second surface 1350 in this mid portion is oriented upwardly, and the first surface is facing downwards. In order to avoid collision of a left with a right support plate, they may be operated with a certain offset in timing, or they are slightly offset in their z-directional positioning, or the one or both of the rotating plates may be slightly shorter than material 1210 affixed to them. Through this, an overlap between the front left and right and rear left and right portions of material 1210 can be achieved. Upon connecting the overlap portions such as by permanent or releasable forming of a bond e.g. in a bond region 1030, a hoop structure as can be seen in FIG. 1 is formed.

This buckling and turning of the centre portion 1215 is a geometric effect, and within wide ranges independent of the material properties. Thus, this buckling and folding can be achieved with relatively rigid materials, such as writing paper, or relatively supple materials, such as non-woven materials or paper tissues. Accordingly, also elastic materials or material composites may be used. In particular, materials typically applied in the manufacture of garments or absorbent articles, such as the backsheets, topsheets, elastic nonwovens, but also absorbent web materials, and the like, perform well in such an operation.

In FIGS. 2E and 2F, the outward rotation is explained, such as may be suitably used for forming pre-forms for two hoops. FIG. 2E shows the corresponding view to FIG. 2B, except that the rotating axes are positioned inwardly of the support plates. After affixing the hoop materials onto the support plates, these are now rotated such that the first (here rectangular) sections with the front and rear portions of the hoop materials are turned outwardly such that the mid portion 1215 of the hoop material is buckling and inverting. Thus in this case, no complete hoop is formed, but only a pre-form, which may be used to form a closed hoop such as by appropriate folding and connecting or by addition of a further material (not shown).

Optionally, these two executions may further comprise the step of providing a further material, such as a cut piece of a web material, which may fit into the opening of the hoop 1001. When the hoop is adapted to form a head-band, the additional piece may cover the head of the wearer, and the article may be a cap. An additional material may also bridge the space to close the hoop of a pre-form according to FIG. 2F.

FIG. 3 shows an article, as may be manufactured by combining various hoop or hoop pre-form making processes. A pants structure as schematically shown in FIG. 3 comprises a waist encircling hoop, here with one connecting line 1030 positioned in the front waist region of the wearer whilst the second one in the back region is not shown. The pants further comprise a left and right leg hoop 1230, and a front (1092) and a rear (1098) pant piece, which may be connected in the hip region of the wearer along a connecting line 1030.

In FIG. 4, a loincloth article as not being within the scope of the present invention 1200 is shown, which comprises a waist hoop 1220 and in addition thereto a centre piece 1010 which is adapted to be positioned with its crotch region 1015 in the crotch region of a wearer, and which is connected with its front (1012) and rear (1018) portions to the waist hoop. The centre piece may be a simple web material such as cotton weave or a nonwoven web of synthetic or natural material, and thus the articles may be simple disposable underpants. The centre piece may also be an absorbent member, optionally releasably connected to the waist hoop, and thus the article may be a simple fully or partly disposable article such as a diaper, such as being well known in the art (see e.g. WO 08/093271).

FIG. 5A shows schematically a perspective view of an article which suitably can be produced by a method according to the present invention. The article 1000 comprises a centre piece 1010 comprising a front waist region 1012, a crotch region 1015 and a back waist region 1018 corresponding to the regions of the wearer during use. The article exhibits generally a length direction 1020—defined by the sequence of front, crotch, and rear regions, and a width direction 1021 of this article perpendicular thereto, essentially aligned with a left—right orientation on the wearer. A thickness dimension extends perpendicularly to the length and width direction, whereby a surface, which is oriented towards a wearer during use is referred to as the "inner" surface 1050, and the opposite one as the "outer" one 1070. For absorbent articles, also the terms "topsheet" as the user side surface 1050 and backsheet as the outside 1070 are used in this context, and an absorbent core (not shown) may be positioned there between. For a single sheet or web of material having essentially two opposed surfaces extending in the x-, y-dimension and a relative small thickness extension, a first surface may be called "topsheet oriented" or "inner" surface, when this surface is oriented towards the body of the wearer during use, even if this surface may be oriented downwardly on the manufacturing equipment during the manufacturing process, or even if this surface is outwardly oriented during the process and inverted (i.e. turned "inside out") prior to packaging or use.

The centre piece 1010 may be a unitary structure, although often it will be composed of various materials, such as backsheets, topsheets, absorbent cores embedded between topsheet and backsheet, so called secondary topsheets, barrier leg cuffs, absorbent elements, closure elements and the like, all well known to a skilled person.

During use, the article may be in a closed loop (or hoop) arrangement around the waist of the wearer. Whilst the present invention has been described by referring to a "topsheet" and a "backsheet" side for distinguishing the first and the second surfaces of a web or a composite, the web may be a single layer (such as a non-woven web, or a film), a composite of alike structures (such as dual layer web), or a composite of other structures, such as the topsheet, core and backsheet composite. Such a composite may be made up of webs only, i.e. of essentially continuous materials, or a sequence of cut pieces of such an essentially continuous material. Such a composite may also comprise structures typically not understood as webs, such as air laid cores, snap fastener, and the like.

As shown in FIG. 5A, side panels 1250 may be connected to the centre piece 1010 and/or to themselves, either permanently or releasably. Thus, the articles may be fully closed pants, pre-closed pants, which may be opened by the user, or may be an open pad which may be closed e.g. by adhesive tapes or so called mechanical fasteners around the waist of the wearer, as typically done with conventional baby diapers or adult incontinence articles, and optionally around the legs of the wearer.

In the present context, pants or pants-like structures comprise leg hoops, i.e. closed structures 1100 encircling the legs of a wearer during use, whereby a surface of the hoop, which is in oriented towards the body surface (either the inner surface, or the outer surface, or both, if the hoop is folded along a fold line running circumferentially around the leg onto itself) retains this orientation throughout the hoop.

Within the current context, the term "hoop material" refers to the materials 1210 which may be connected by a connecting or fold line 1130 to the crotch or mid region of the centre piece. As described in the hereinabove referenced recent C-4-S publications, the connecting may be achieved by a curve-linear connecting line 1130. Alternatively, the connecting may be achieved by a connecting region with curve-linear boundaries. Yet in a further alternative, the connecting may be along a straight connecting line, but a curvilinear folding line will be formed during use adjacent to the connecting line. This will—even when performed in the flat state during manufacturing—create a three dimensional (3D) body conforming structure upon donning of the article. The connecting can be performed by various connecting means, such as thermo-, pressure-, or ultrasonic-bonding, or by application of adhesives or glues, as well known in the art. The hoop material 1210 may be connected to itself, such as by a permanent or releasably closed connecting means, in the figure shown as a connecting line 1230.

Figure 6A:
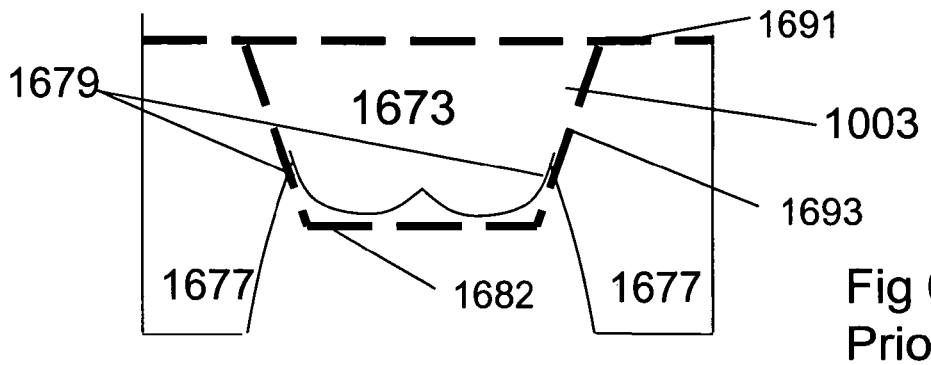
FIG. 6 A-D show a schematic view of conventional designs on a wearer.
Figure 6B:
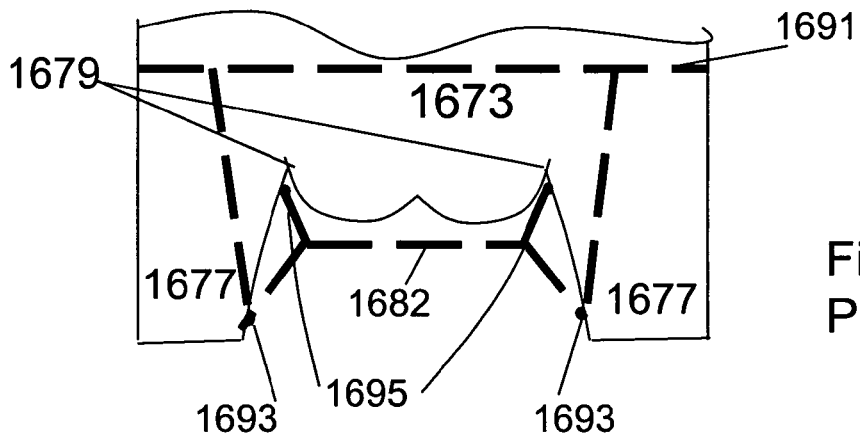
Figure 6C:
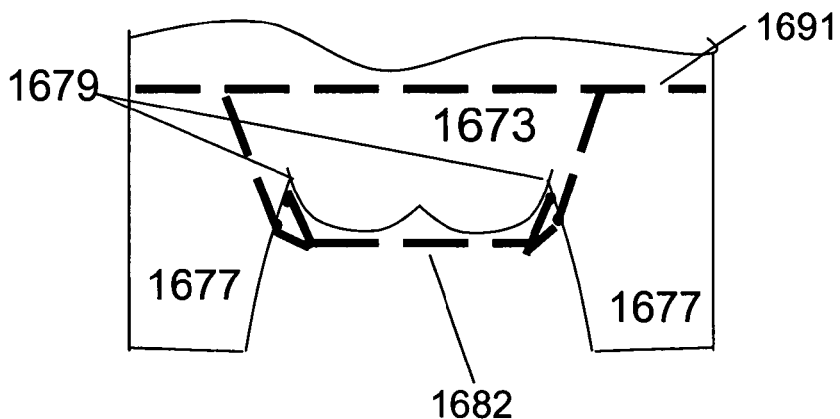
Figure 6D:
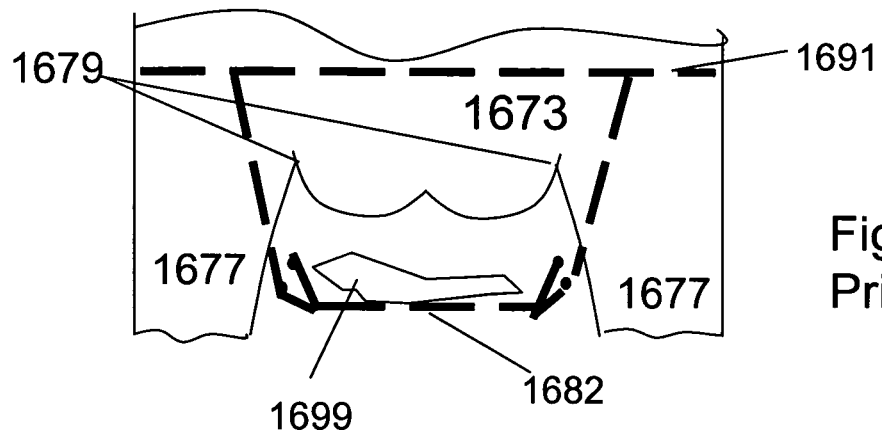

Thus, the body conforming articles as described in the above mentioned recent publications in the name of C-4-S and as being subject of the present invention fit very differently, compared to conventional articles. As shown in FIGS. 5B and 6A, such conventional articles 1003 are primarily supported and held on the body by a waist encircling hoop 1691, as may be the waist circumference of pants products, such as training pants, or which may be formed of the front and rear longitudinal end regions, which may be connected such as by tapes or other closure means in the lateral front regions of the article. The article further comprises a centre region 1682, which is typically made of absorbent material and so called leg elastics 1693 positioned along the lateral side portions of the article running from the front region through the crotch region to the rear region, which pull the lateral edges of the article into the crotch crease 1679 between the legs 1677 and the lower torso 1673 of the wearer. Often, such articles further comprise so called barrier leg cuffs (BLC) 1695. Upon donning, the article is expected to be applied as indicated in FIG. 6B such that the leg elastics 1693 fit lower on the leg of the wearer and the BLC elastics fit into the crotch crease. Because the leg elastics cause a significant contraction in the region where they are attached to the article (i.e. in the leg cuff region), and because the article is significantly less contracted in the core region, a bowl shape is assumed. This bowl shape, however, is not a 3D-shape in the meaning as used for the body-conforming articles discussed herein, as it can be laid out completely flat on a plane by merely extending the elastics (after opening the article or cutting it open along two imaginary cut lines positioned in the regions of the article, which correspond to the lateral regions of the wearer, such as the left and right hip regions, and being essentially parallel to the longitudinal direction of the wearer). However, as the leg elastics are primarily longitudinally oriented they will pull the leg elastics upwards (relative to the wearer) and will also move into the crotch crease as indicated in FIG. 6C. When the article is loaded with urine and/or with faeces 1699, the weight can pull the centre region downwards and leakage can occur (see FIG. 6D). Typically, however, this risk for leakage is further aggravated by the so called "sagging" effect, which describes the downward slippage of the waist hoop region due to the combination of gravity and the pull-down forces of the elastics.

Figure 6E:
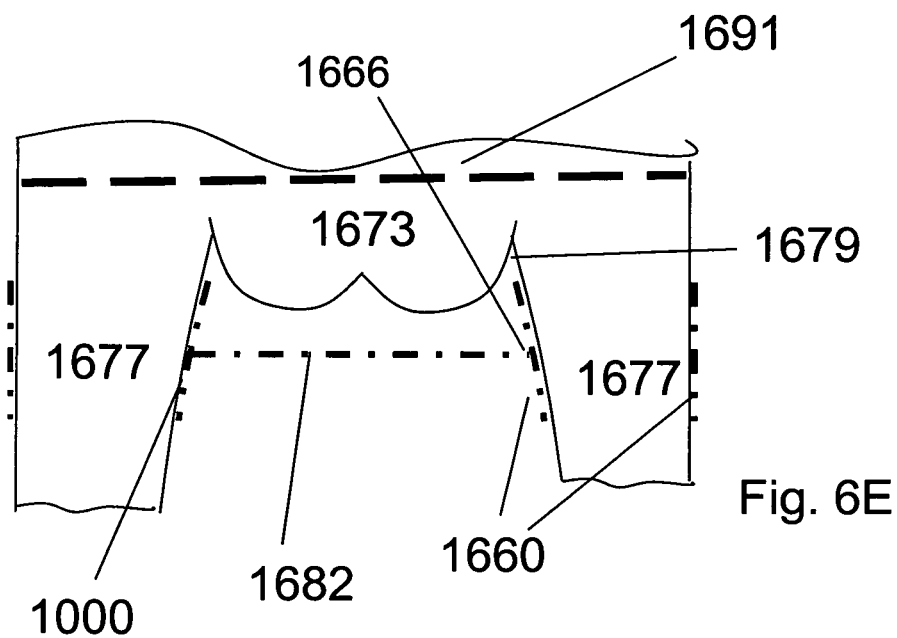

Also, as shown in FIGS. 6C and 5B, the lateral outer edge of such conventional articles is unavoidably twisted in the crotch crease region, further enhancing the stress of the leg elastics and increases the risk of redmarking in the transition region 1697 from the elasticated parts 1005 in the crotch region to the elasticated or nonelasticated parts of the side panel material 1250 as indicated. All articles as described in the recent applications in the name of C-4-S as well as articles as described herein exhibit a curvilinear connecting or fold line or region in the leg hoop region or adjacent thereto in the centre crotch region. In a simplified view of reducing the legs to cylinders having an upwardly oriented longitudinal centreline and of reducing the lower parts of the torso to a section of a cylinder having its longitudinal centreline essentially perpendicular to the ones of the leg cylinders, this curvilinear line corresponds to the line of intersection of these cylinders. It is the particular interaction of the leg hoop with this curvilinear line that creates the particular three-dimensional body conforming cup shape of the article. Thus, during use the cup shape of such pant like articles can be described by an upwardly opened cup shape in the crotch region cooperating with the leg hoops, which are outwardly adjacent to the centre crotch region and connected thereto by a curvilinear connecting or fold line or region. Thus along this curvilinear line (and only along this line or at least for transition of the leg hoop centre portion to the side panel region), a "Y-bond" 1666 (as can be seen in FIG. 6E) connects the leg hoops with the centre piece. A further feature of the 3D body conforming cup shape can be described when considering such a pant like article being cut open. In the case of openable diapers (such as for baby diapers or adult incontinence articles) the opening will correspond to opening the tapes or other closure elements of the article. In the case of closed pants structures (such as so called training or incontinence pants) this opening may occur along two imaginary cut lines positioned in the regions of the article, which correspond to the lateral regions of the wearer, such as the left and right hip regions, and being essentially parallel to the longitudinal direction of the wearer. After the (real or imaginary) opening of the article, the article can only be laid flat on a plane, if (and only if) at each side at least the leg hoop and or the side panel material is folded onto itself, i.e. along a 180° fold line. In a "reverse engineering" consideration, this can also be described when looking at the last manufacturing step just prior to the folding and closing of the article, during which the article is easily handable by being essentially flat, but when folding the article to form a closed hoop structure, the leg hoop and/or side panel material is folded onto itself, and upon donning of the article the 3D body conforming cup shape unfolds. In this context, even if the leg hoops are designed to be contractible or made of an elastic material to allow adaptation to varying dimensions of different users, this extensibility or elasticity is not essential for creating the 3D body conforming cup shape.

For certain product embodiments such as described in the PCT'3844 application, parts of the leg hoops, which extend forwardly and rearwardly before the flipping, are folded over themselves along a fold line which may be oriented at about 45° relative to the longitudinal centre line, such as to extend outwardly after the flipping. As prior to the flipping the leg hoop material was positioned essentially flat on a support medium, a first surface being in contact with this support, i.e. being oriented downwardly, remains in contact in the centre region, whilst in the outwardly folded portions this surface is now facing upwardly.

Such embodiments of the body conforming articles form a smooth hoop around the upper thigh region of the leg of the wearer, without any twisting, and thus it is always and essentially only one surface—e.g. the topsheet surface—contacting the skin. Referring to FIG. 6E, the article 1000 is supported by the leg hoops 1660, and the waist hoop 1691 does not need to carry all the weight of the article. The sealing function is achieved by a smooth sealing surface, rather than the often corrugated or even crumpled line seal of the conventional design. The folding over of the leg hoop during the manufacturing will essentially unfold upon application of the article, and the full hoop will be upwardly positioned in such a way, that the previously outer lateral edge of the centre region will be oriented towards the crotch crease of the wearer. If articles such as absorbent articles such as diapers have distinctive surfaces such as in the latter case an inner or topsheet side and an outer or backsheet side, it is advantageous if all surfaces which are in direct contact with the skin of the wearer are made of skin friendly material. However, as can be seen in FIG. 5B, conventional diapers contact the skin in the upper inner thigh region with their back sheet side. The application of the method according to the present invention as described hereinafter allows easy manufacturing of articles with a leg hoop contacting the skin with the same material surface as in the crotch region. The present invention relates to a process alternative to the processes as disclosed in the recent applications, significantly easing the manufacturing and the equipment design to produce both articles as described in the recent applications as well as such new articles.

In particular in the PCT'3844 application, a process is described, which "flips" the leg hoop material by means of a rotating support plate to which at least parts of the material are affixed. Before flipping, the leg hoop material is essentially oriented parallel to the manufacturing direction (MD) of the centre piece, to which the leg hoop will be attached. This MD is also aligned with a front to back orientation through the crotch region of a wearer during use. The rotation of the rotating support plate occurs around a rotating axis, which is essentially co-planar with the plane of the centre piece and also the leg hoop material before flipping. The rotating axis is further positioned at an angled orientation to the MD, typically at an angle of between 0° and 90°, preferably of between 45° and 60°.

This process is further explained with FIG. 7A showing such an article 1000 prior to the flipping step in a top view with two cross-sectional views AA and BB respectively. The article 1000 is schematically shown with a rectangular topsheet 1050 and an essentially coextending backsheet 1070 with a length (1020) essentially aligned with the machine direction of the manufacturing unit and width (1021) orientation. As shown in FIG. 7A backsheet 1070 is facing upwards, such that the oppositely positioned topsheet 1050 is in contact with the centre piece support means, such as the surface of a rotating drum (not shown in the figure). An absorbent core 1060 is indicated in a moderate plus-shape (hatched lines in the top view) in between topsheet and backsheet. Also shown are four cut lines 1150 extending from the front (1032) and rear (1038) edges essentially parallel to the side edges 1035, and terminating in the mid region of the article. These lines delimit the leg hoop materials 1210 from the centre piece 1010 of the article.

Figure 7B:
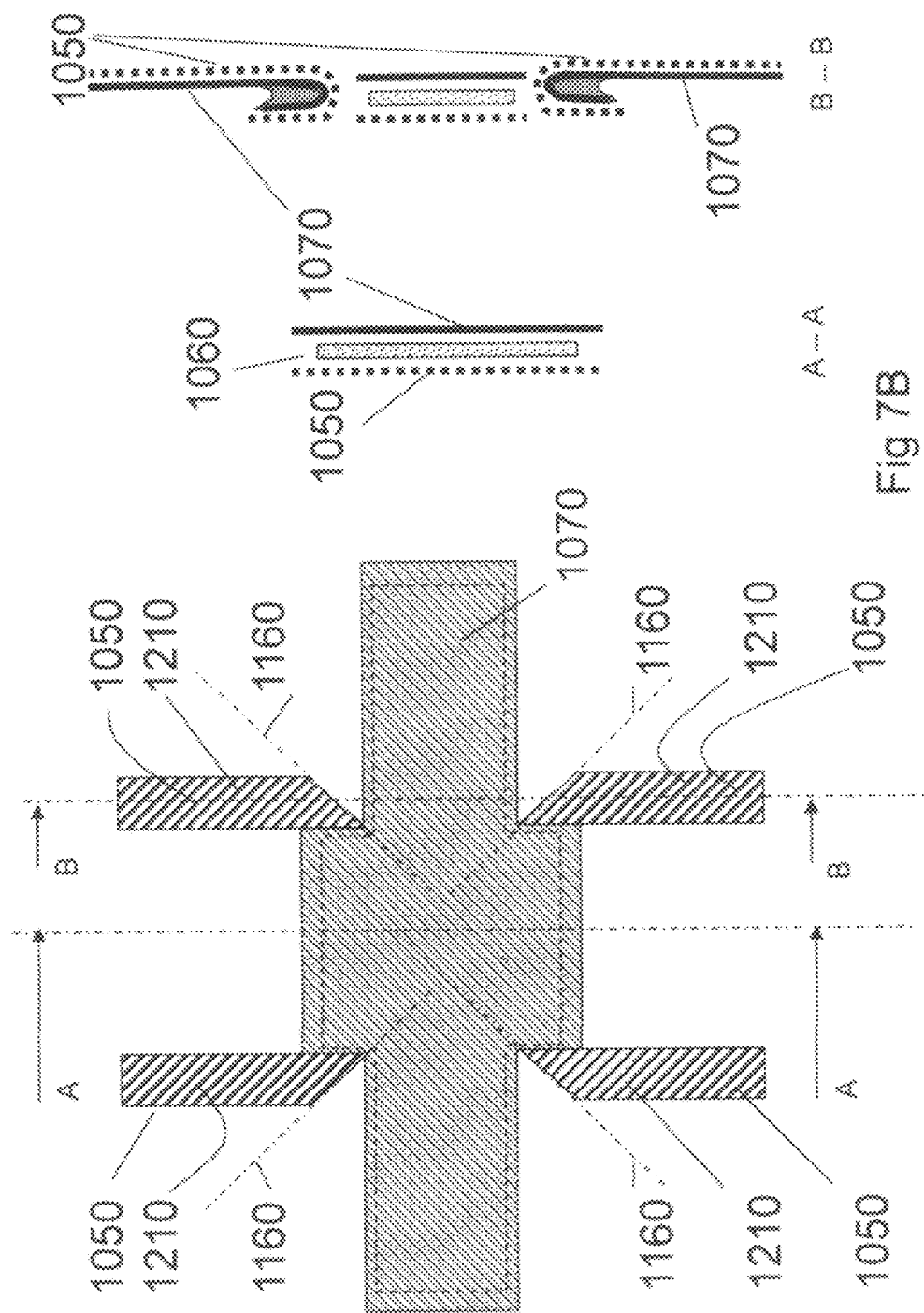
FIG. 7 A-C show an article as known from recent prior art at stages throughout its manufacturing process.

FIG. 7B shows the article after the flipping step. To this end, the four leg hoop areas 1210 are flipped by means of rotatably mounted flipping plates (not shown) by 90° around folding lines 1160 positioned in the length/width plane at an angle of 45°, such that they extend now outwardly sideways. In the flipped portions, the topsheet 1050 is now facing upwardly.

Figure 7C:
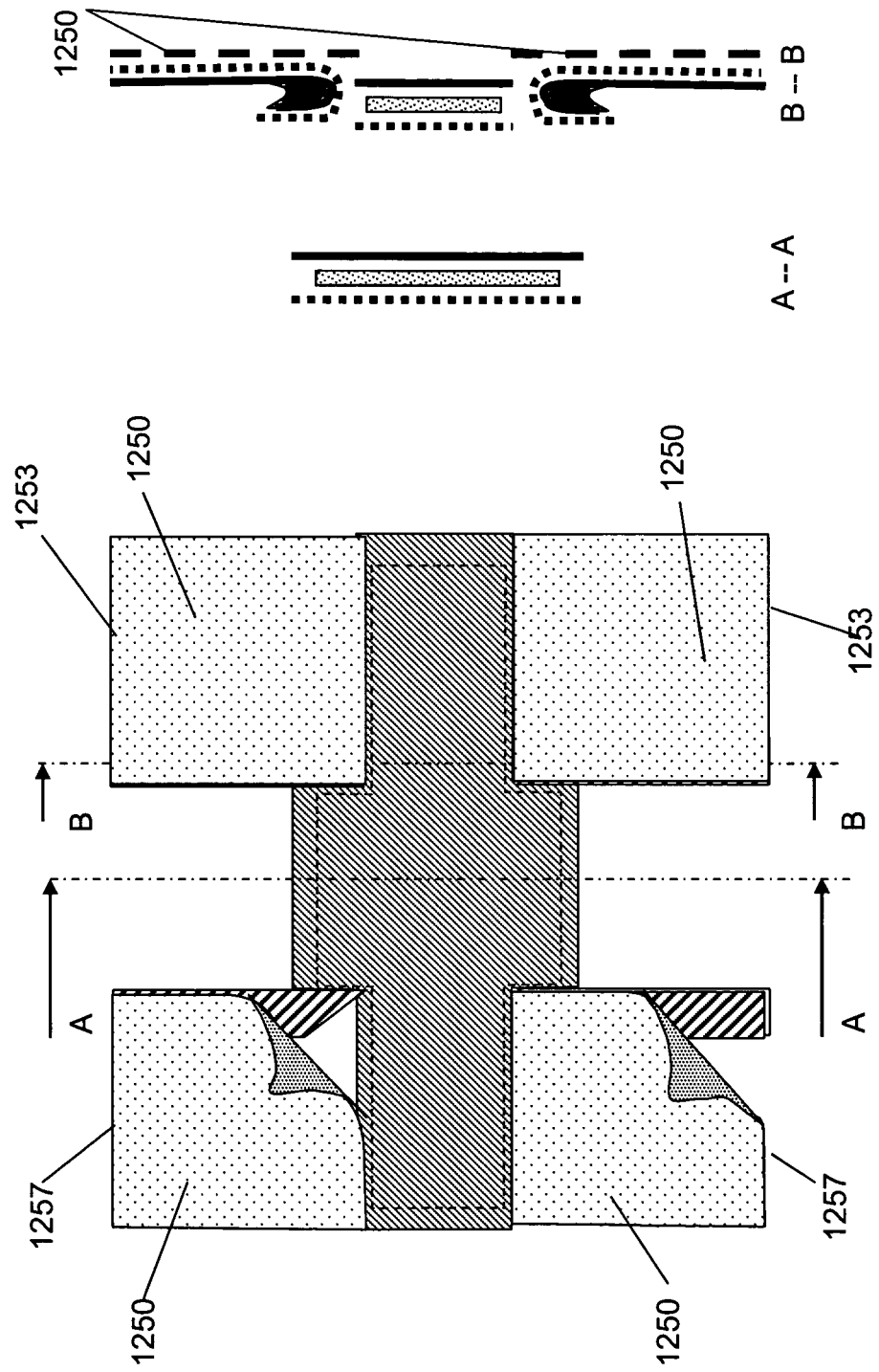

Side panel material 1250 may be added as shown in FIG. 7C by conventional means. When the front (1253) and rear (1257) lateral edges of the sidepanels 1259 are connected, a pant structure with a 3D body conforming fit results. Alternatively, the rear and front sidepanels may be designed to overlap and may be connected with conventional means such as tapes or mechanical fastening means. Whilst this figure shows the particular embodiment wherein the leg hoop materials are cut from a unitary leg hoop and centre piece material, the same basic mechanism of folding and flipping applies to the other embodiments.

Whilst the process and the product as described in the PCT'3844 application show particular advantages for certain applications, the present invention provides an alternative with regard to the process and with regard to certain resulting products.

Similar to the PCT'3844 process, the process according to the present invention includes rotating the front and rear portions of the web material sideways inwardly or outwardly, but in contrast to the PCT'3844 process, this is achieved by a rotation around an axis which is essentially perpendicular to the surface of the hoop piece that is to be rotated.

The general functioning of this mechanism is explained by referring to FIG. 8, showing schematically an article 1000 with a centre piece 1010, having an upwardly facing backsheet 1070, an essentially coextensive oppositely positioned topsheet 1050, and an absorbent core 1060 therein between. In the shown embodiment, the leg hoop is formed from a separate material 1210 made of topsheet material 1350 and a backsheet material 1370, optionally elastics, optionally an absorbent layer between the top- and backsheet layers, or a single layer with a top- and back side. The centre piece may be positioned on a centre piece support means (not shown), which may be—as described in PCT'3844 in more detail— the surface of a rotating drum. For the configuration as shown in FIG. 8A, the topsheet material is in contact with the centre piece support means surface (not shown), whilst the backsheet side is facing up.

In addition, FIG. 8 A shows four support plates 1310 as described in the context of FIG. 2, each one for the front/rear and left/right leg hoop portions (one shown with the leg hoop material lifted up, the other ones shown as being slightly larger in size than the leg hoop material). These support plates are suitably connected to the centre piece support means. They are mounted so as to allow rotation around axes 1320 which are essentially perpendicular to the surface of the plates (i.e. also to the drawing plane). The rotation may be driven by conventional drive means, such as digitally programmable drives or servo drives or cams or pneumatic cylinders etc. . . . . The support plates are shown having a trapeze shape, tapering as from their rotation centre towards the centre region at a 45° angle along lines 1160. One strip of leg hoop material is provided such that its first (front) extension or region, mid region and second (rear) extension or region are aligned along the machine direction of the manufacturing equipment and laid on each side of the centre piece onto the front and rear support plates and affixed thereto by conventional means such as vacuum suction means, which may also be programmable, preferably featuring digitally programmable or mechanically adjustable shut on and shut off points. Optionally, the strips of material are slightly overlapping the centre piece material and may be attached thereto in the crotch area. As shown, a first surface of the leg hoop material, here shown as the backsheet 1370 is facing upwards, whilst the opposite surface, here shown as a topsheet 1350, is facing towards or is in contact with the support plates 1310. Thus, each strip of hoop material can now be seen as having three portions, the front portion 1212 as overlying the support plate which is positioned towards the front edge 1032 of the centre piece, an oppositely positioned rear portion 1218, and a mid portion 1215 there between, which may remain essentially unsupported. As indicated, adhesive glue lines 1130 may be applied in the mid portion 1215, onto the upward facing surface 1370 of the leg hoop material, but may also be applied to the front or rear portions (1212 and 1218, respectively).

Figure 8C:
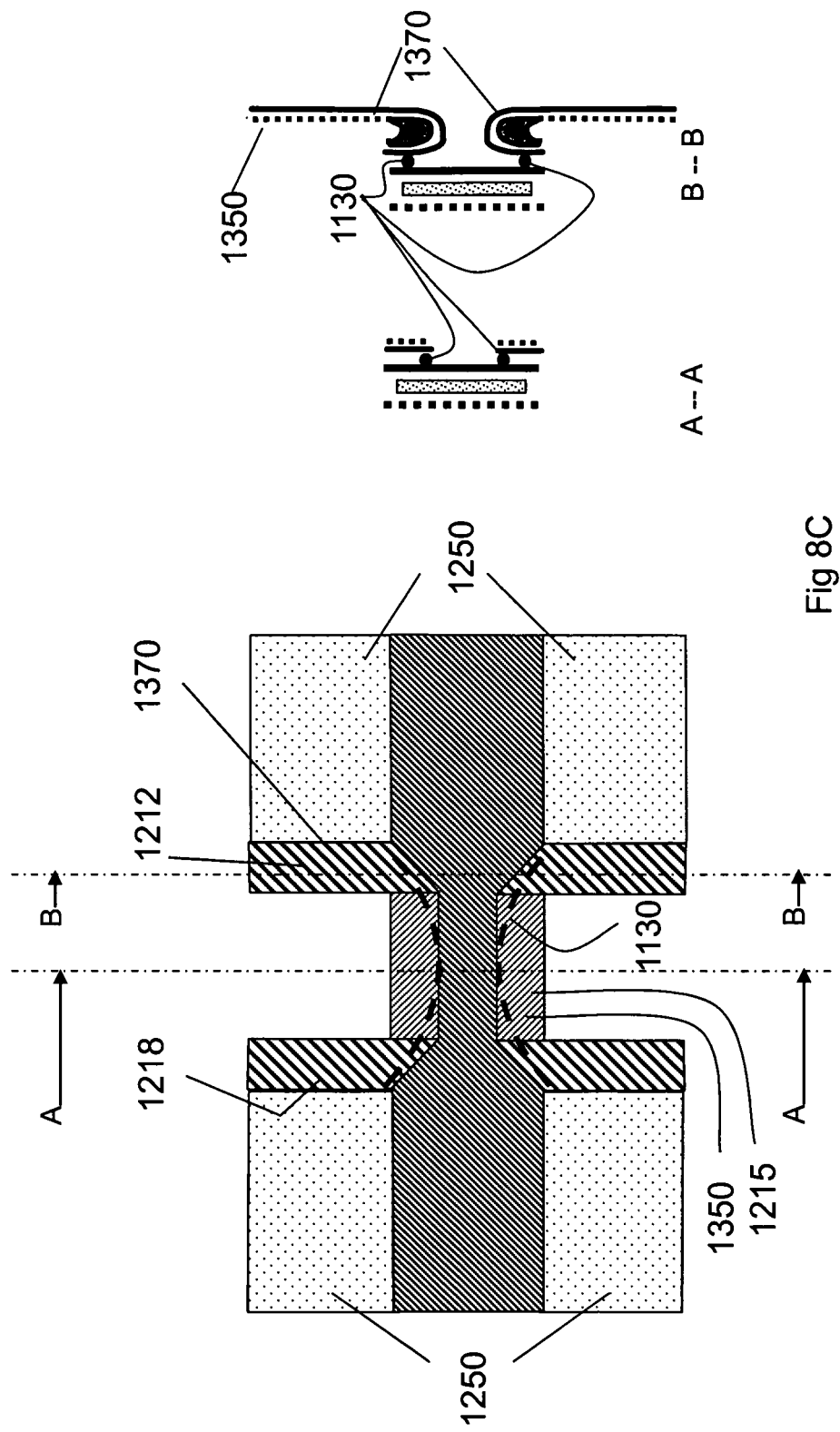
FIG. 8 A-C show an article at stages throughout its manufacturing process according to the present invention.

Now the support plates 1310 are rotated around their axes 1320 by about 90°, such that their first sections are oriented outwardly (i.e. cross directionally), whilst the tapering second sections 1313 turn over the centre web. As the leg hoop material remains affixed to the support plates in the front and rear portions, also the front (1212) and the rear (1218) portions of the hoop material will turn outwardly, with their upward backsheet surfaces 1370 remaining upwardly oriented. The unsupported mid portion 1215 will inevitably buckle upward or downward and turn or fold over itself, such that now the second topsheet surface 1350 in this mid portion is oriented upwardly, and the first surface 1370 (onto which the adhesive line 1130 may have been applied) is facing downwards. Also for this embodiment, a sidepanel material 1250 may be added, such as shown in FIG. 8C.

Optionally, the buckling and turning of the centre portion may be supported or directed (e.g. towards "upward" or "downward") by mechanical means. One suitable embodiment is shown in FIG. 8D to 8F, showing schematically a perspective view of a support plate 1310, which is segmented in to a first section 1312 and an second section 1313, connected by a hinge means 1311. The second section 1313 is connected to one end of a curved lever 1316, whilst the other end of the lever is affixed to a lever support 1317, on a joint base plate 1314 for the lever support and the rotation axis 1320. The rotation axis 1320 is connected to the first section 1312 of the support plate next to the hinge means. As shown in FIG. 8E, upon rotation of the support plate around the axis, the curved lever will lift the tip of the second section of the support plate upwardly, thusly supporting the buckling and turning of the centre portion of the leg hoop material. After a 90° turn, the tip of the lever will be in a lowered position again and the second section 1313 will be at level with the first section 1312.

Figure 9C:
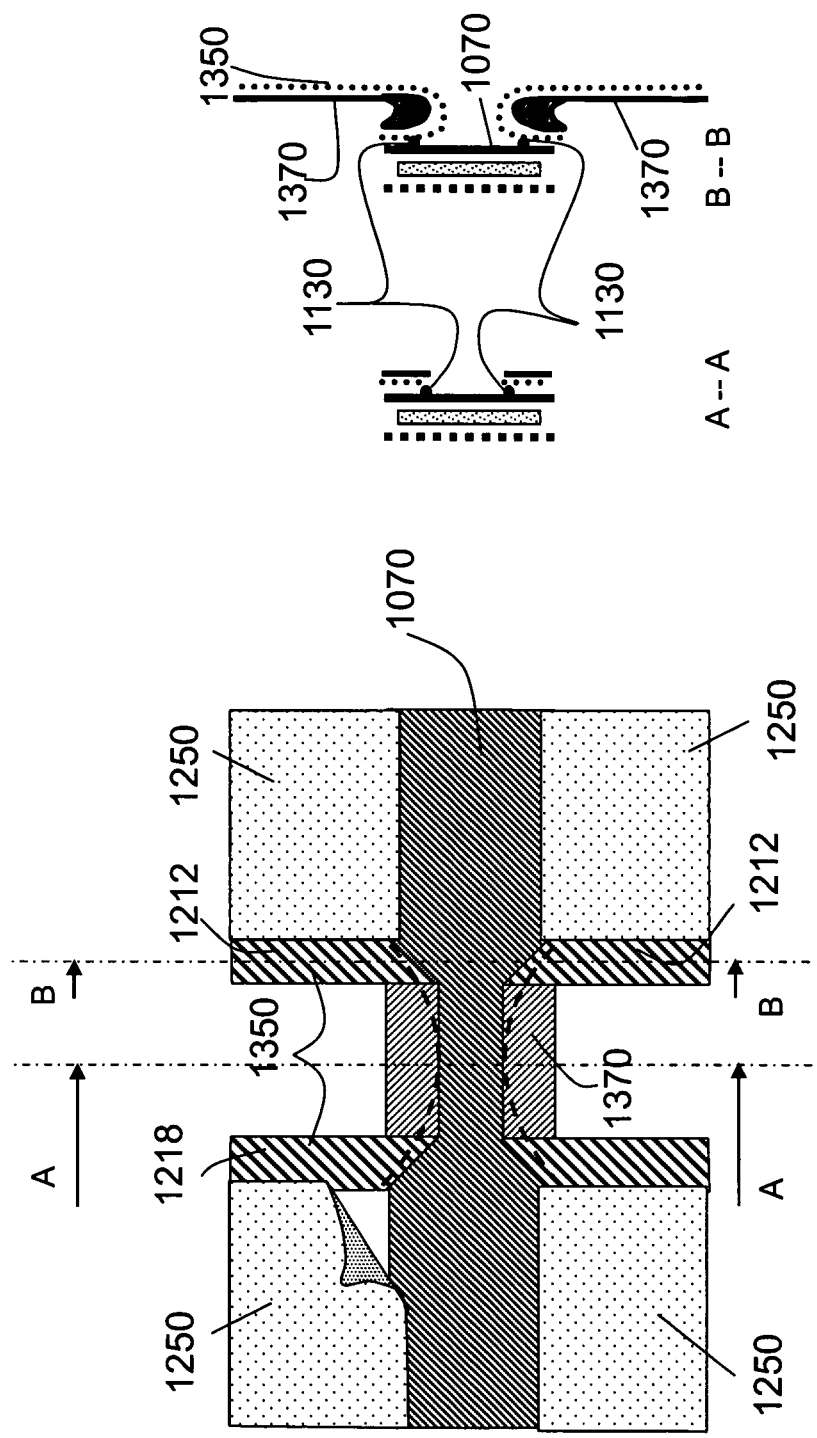
Figure 10C:
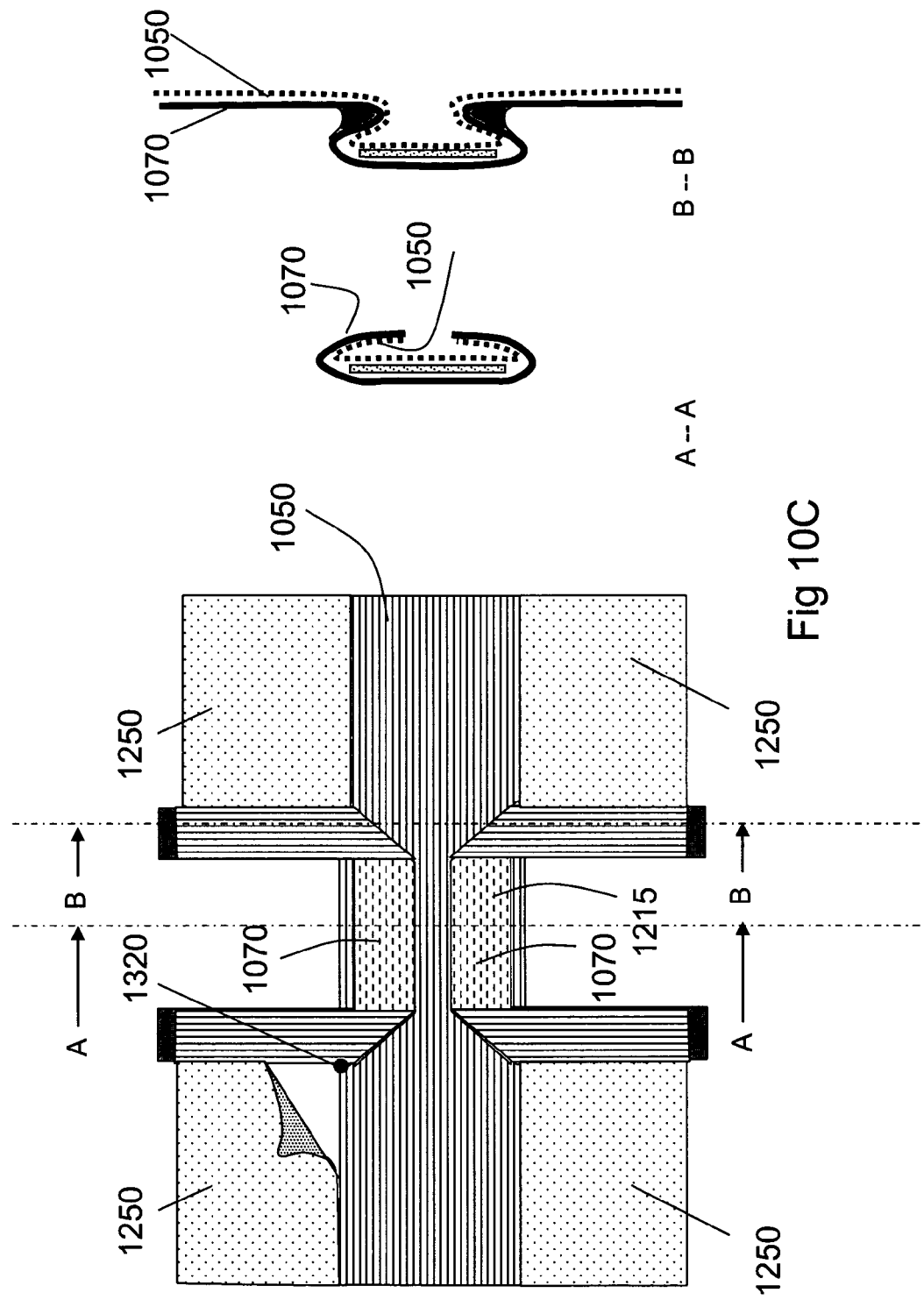

FIG. 9 depicts an article, which may be manufactured by a method according to the present invention, where the leg hoop material 1210 is initially positioned "upside down" as compared to the one described in FIG. 8, whilst the centre piece material has the same orientation. Whilst the topsheet side 1050 of the centre piece 1010 will be oriented towards the support means, and the backsheet surface 1070 will face upwardly, the leg hoop material is provided such that its topsheet surface 1350 is facing upwardly, and its backsheet side 1370 towards the support plates. Consequently, after rotating the first (front) 1212 and second (rear) 1218 hoop extensions or regions outwardly, thusly inverting the mid or centre portion 1215, the relative positioning of the backsheet and topsheet surfaces in the centre portion and the leg hoop portions is changed versus FIG. 8. The present invention further relates to the manufacture of a product, where—similar to the embodiment as described in the context of the PCT'3844 application—the leg hoop material is not a separate material, but also supplied unitary or integral with the centre piece. As shown in FIG. 10A and in contrast to the execution as shown in FIG. 7, the topsheet side 1050 is facing upwardly, whilst the backsheet side 1070 is facing towards the centre piece support means (not shown) and the leg hoop support plates 1310 (shown in the cut out sections). Similarly to the article as shown in FIG. 7A, separating lines such as cut lines 1150 extend from the front (1032) and rear (1038) edges towards the centre region. The separation lines may also be in an angled arrangement relative to the MD-line, and may even intercept the outer periphery of the article in the lateral side margins, as long as this intersection is positioned longitudinally outwardly of the end point of the separation line. Thereby nine segments are defined, namely a front and a rear region of a centre piece each positioned laterally between two separating lines;

a crotch region of the centre piece positioned between the front and rear regions;

a first (front) 1212 and a second (rear) 1218 hoop extension or region of the first and second hoop material each positioned laterally outwardly (relative to the longitudinal centre line) of the separating lines 1150;

and one mid or centre hoop region or portion 1215 for each of the first and the second hoop material, positioned longitudinally between the front and rear portions and laterally outwardly of the crotch region of the centre piece, The portions 1212 and 1218, which extend outwardly of these cut lines correspond to the front and rear leg hoop portions, and are affixed to the leg hoop support plates 1310 (see cut-out sections in FIG. 10A). These are now—in analogy to what has been described in the context of FIG. 8—rotated by 90° around their axes 1320, such that the front (1212) and rear portions (1218) extend outwardly as outer leg hoop portions, whilst the portion 1215 between these now form the mid portion of the leg hoop. Whilst the front and rear portions retain the z-directional orientation (i.e. topsheet surface 1050 facing up), the material in the centre leg hoop portions is inverted, here now with backsheet surface 1070 facing up.

A further execution of the present invention is explained in the context of FIG. 11. In this execution, a side panel material is integral with the leg hoop material, rather than being supplied as a separate material as for the embodiment as shown in FIG. 9C. To this end, U-shaped materials 1400, as indicated in FIG. 11A, are supplied, each having prior to the rotating step (d) essentially CD oriented front and a rear portions and an essentially MD oriented connecting portion, which may be cut out of a single web, such as explained in more detail in PCT'3844. The integral hoop/side panel materials and the centre piece are registered and arranged such that prior to the rotating step (d) the first and the second U-shaped integral leg hoop/side panel materials are positioned essentially symmetrically to the centre line with the opening of the U-shape being oriented towards the centre line (both of the manufacturing equipment and of the article). Portions of these materials are—before they are combined with a centre piece—rotated relative to a symmetry line 1410 of the article aligned with the MD centre line of the closed loop operating means 1305 in analogy to what has been described above around axes 1320, such that a mid hoop portion 1415 is inverted "upside down", whilst the first and second hoop extensions, which are integral with the side panel portions in the front (1412) and in the rear (1418), respectively, retain their upward facing surface orientation. As shown in FIG. 11A, the backsheet side 1470 of the hoop material may face upwardly. As can be seen in FIGS. 11C and D the backsheet side 1470 will still face upwardly in the front and rear portions also after rotating, whilst in the centre portion the topsheet side 1450 faces now upwardly. As shown in FIG. 11D, this material may then be combined with the centre piece material 1010, here shown to be affixed onto the backsheet side 1070 of the centre piece.

A particular aspect of the present invention relates to an embodiment, wherein the axes for rotating the leg hoop support plates are not only rotatably mounted (to allow the rotation) but are further translatorily moveable connected to the centre piece support means, such as to the rotating drum. This translatory movement can be essentially parallel to the MD direction 1020 of the manufacturing equipment and/or the CD direction whilst the orientation perpendicular to the MD/CD plane may remain essentially unchanged. Such movement may improve both size and design flexibility of the equipment, but it also provides means to execute specific features of the product. In case of an essentially translatory motion in MD, it allows stretching of selected regions of an elongatable, e.g. an elastic leg hoop material, as can be seen in FIG. 12. When starting, for example from the situation as shown in FIG. 8A, the support plates having the front (1212) and rear (1218) leg hoop portions attached thereto, are moved away from each other, so as to increase the distance between these portions and thusly extending the mid leg hoop portion 1215 without extending the front and rear leg hoop portions. In FIG. 12, the centre piece 1010 is shown with the leg hoop material 1210. The front and back portions are shown in their original positioning as 1212 and 1218, respectively. After the axes 1320 are moved into the positions 1320', the front and rear leg hoop portions are shown in the positions 1212' and 1218', whilst the mid leg hoop portion 1215 is extended to the longitudinally offset borderlines 1215'.

Figure 13A:
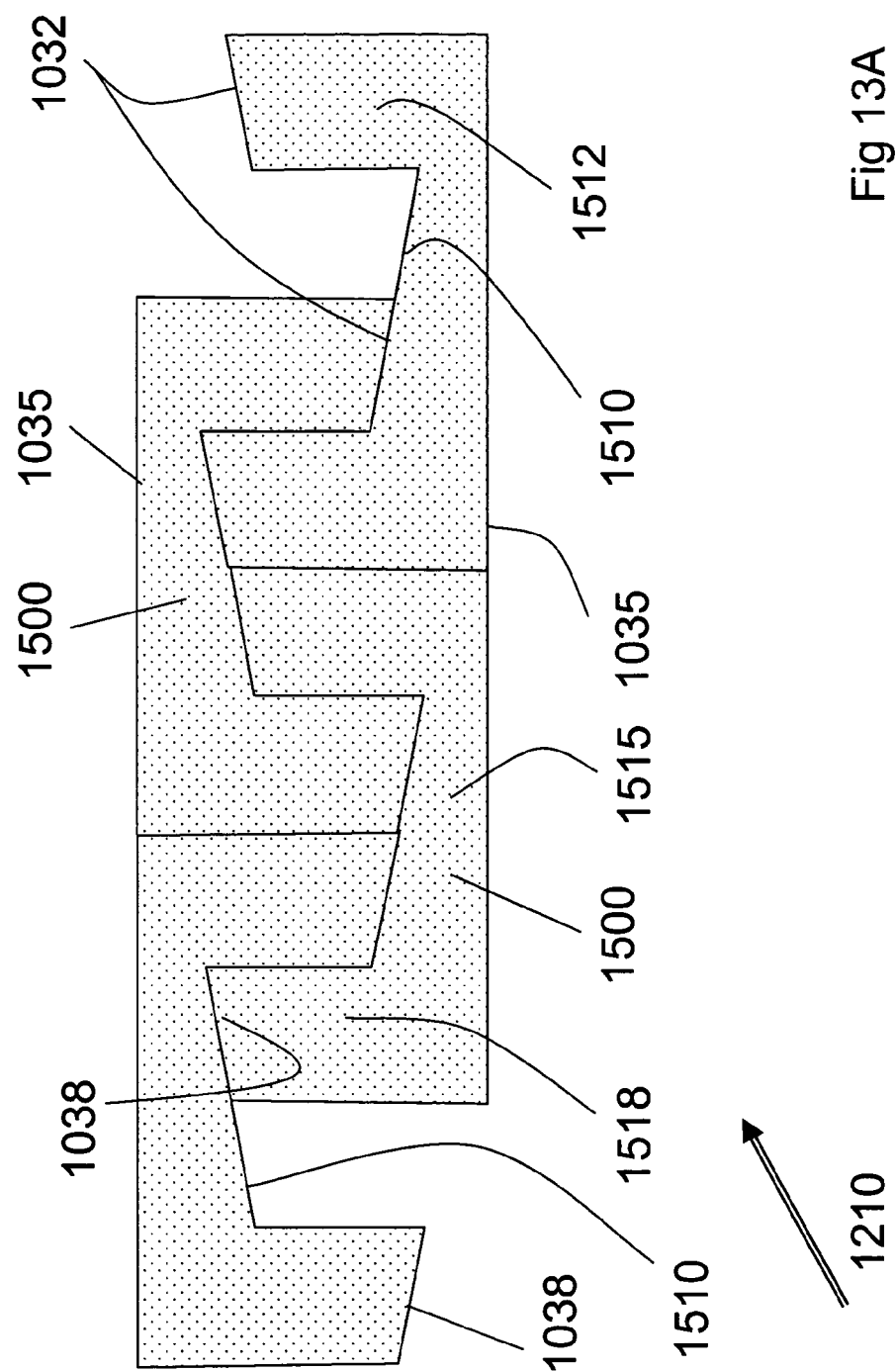
FIG. 13 A-D illustrates the making of an article with an asymmetric fit on its wearer.

Yet a further embodiment relates to the making of an article showing an asymmetric fit on a wearer. This refers to e.g. pants, for which the front region fits lower than the rear region, i.e. the front region is shorter (than the back region) relative to e.g. a fold line in the crotch of the wearer during use. To this end, a combined side panel/hoop material is not separated symmetrically, but in a meandering pattern such as along a cut line 1510 as shown in FIG. 13A, separating front (1032) and rear (1038) lateral edges of the first (front) hoop 1512 and the second (rear) 1518 extensions or portions. As shown, the meandering cut line may include sections, which run essentially cross-directionally, and sections which run predominantly but not exactly in the longitudinal direction.

"Predominantly" refers to an orientation, which has an angle towards the longitudinal line, which is smaller than the complementary angle to the cross-direction. As described in the context of FIG. 11, the now asymmetrically U-shaped combined side panel and leg hoop material 1500 is affixed to support plates, see FIG. 13B. Before rotating, the axes 1320 have a different distance to the product or machine centre line 1410. Then, the axes 1320 are cross-directionally repositioned relative to each other (i.e. either the front, or the rear axis or both) such that they have essentially the same distance to the MD line—as shown in FIG. 13C, the front axis is moved into a position 1320'. The longitudinal side edge 1035 of the material before rotating will change its orientation and will be partly positioned on the centre piece (FIG. 13D). After rotating, the bond lines 1520 and the corresponding connecting line 1530 are positioned so as to allow offset-free combining.

Yet a further and for particular applications preferred embodiment relates to the manufacturing of articles as described in the above, wherein, however, the overall manufacturing direction relative to the introduced materials is changed, such as can be further explained in the context of FIG. 15. FIG. 15 shows a sequence of process steps along the manufacturing machine direction 1620, with the initial situation in the top part of FIG. 15A. There, continuous material 1600 is shown, such as a backsheet 1650 and topsheet 1670 which are most preferably coextensively fed to the manufacturing unit, and may comprise a core 1660 between them. Typically, and as shown in the figure, the core is smaller than the topsheet or backsheet materials, such that these may envelope the core. These elements are positioned on the manufacturing unit such that the front (1612), centre (1615) and rear (1618) regions of the article 1690—when formed from these materials and positioned in its intended use orientation corresponding there to a front to rear orientation along a longitudinal article centre line 1610—are at least initially positioned cross-directionally (1621) on the manufacturing unit with the manufacturing machine direction 1620. To this end, conventional topsheet/and or backsheet materials may be supplied to the manufacturing unit at a width corresponding to the product length during use. An absorbent core 1660 may be supplied by any conventional method or equipment, such as from an online core forming unit i.e. the core making is integrated into the manufacturing line, and the cores may be formed at a speed corresponding to the line speed. Alternatively, the cores may be supplied from an off-line core making unit, either as so called "roll-stock" cores or as "festooned boxed cores", or as single fed items, such as may be provided in cassettes. A combination of on- and off-line core materials into the final core composite is also possible and also well known in the art.

The web materials are predominantly flat, such as typical nonwoven web materials, or backsheet films. Whilst the core materials may exhibit a certain non-flat shape, they extend typically significantly more in the length and width direction of the article than in the z-direction (perpendicular thereto). Thus the materials have a first and a second opposite surface, one of which is oriented towards a surface of the manufacturing unit.

Once the cores are positioned appropriately onto or between the continuous materials, the latter are separated by a first article separation line 1655 such as a cut line, such that the length of the cut material 1625 corresponds to the width of the centre piece 1691 of the article 1690. Two subsequent pieces are now spaced apart along the machine direction 1620 of the manufacturing equipment.

This can be performed by conventional means (not shown), such as described in U.S. Pat. No. 6,544,375 or WO 06/103487, wherein essentially, two subsequent pieces are held to their support in the regions corresponding to the centre pieces of the article, whilst the supports are spaced apart. Next, leg hoop material 1680 is introduced, such as from a continuous supply (not shown). Preferably, the hoop material is supplied with its material machine direction (i.e. the essentially endless direction) parallel to the machine direction of the manufacturing equipment. Upon being cut to pieces having a length corresponding to twice the leg hoop width 1682, it is positioned so as to bridge two subsequent centre pieces. This can be done by conventional "cut and slip" operations, which are well known to a person skilled in the art. In the crotch region of the centre piece, machine directionally adjacent to the positioning of the leg hoop material 1680, glue may be applied to the hoop gluing region 1685, such as by a glue line.

The leg hoops of two subsequent pieces are separated along leg hoop separation line 1667 and the pieces are further spaced apart.

Upon affixing the front (1712) and rear (1718) hoop extension regions to rotation support plates (not shown), the support plates with the extensions affixed are then rotated by about 90° such that the centre hoop region 1715 will inevitably (due to geometric constraints) buckle up and invert its surfaces—indicated by the hatching in FIG. 15D, such that it now overlays the hoop gluing region or line 1685.

In FIGS. 15D and 15E, the spacing of two subsequent pieces is shown so as to allow fitting of side panel material 1750 between centre piece and front respectively rear hoop extensions, such that upon separating the side panels along a final separation line 1722 the final article having width 1725 is composed of centre piece with two hoops and four side panels. In an optional further process steps (not shown) elastic materials 1770 may be introduced such as continuous waist elements. Then, the article may be further folded, provided with closure means such as adhesive tapes or mechanical fasteners, or may also be closed to form a pants like structure by connecting front and rear side margins of the side panels together.

The article as shown in FIG. 15F shows a further particular embodiment for the leg hoop designs, namely that the front leg hoop extension is rotated outwardly by about 90°, whilst the rear leg hoop extension is somewhat diverging from the front one by having been rotated by less than about 90°, here shown for about 83°. This allows further design flexibility for the final article, like a longer rear extension of the product.

Figure 16B:
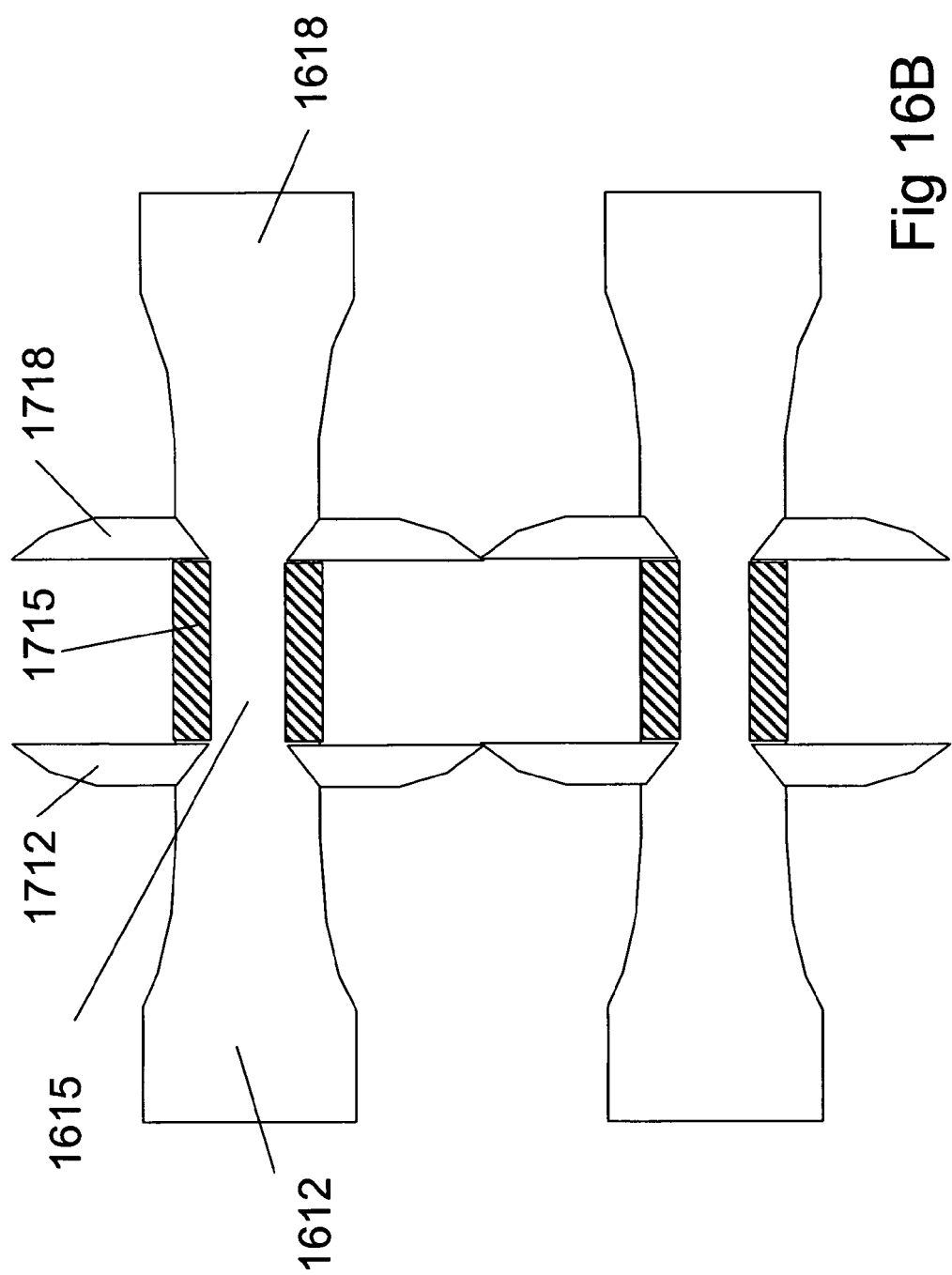
FIG. 16 A-E shows schematically the process steps according to the invention to form a hooped article.

In a further variant of this "CD manufacturing", the leg hoops may be formed as an integral piece of the centre material, as may be further explained by referring to FIG. 16, showing—similar to FIG. 15, a sequence of process steps along the manufacturing machine direction 1620. FIG. 16A shows the continuous centre piece materials such as a backsheet 1650 or topsheet 1670 with a core 1660 between them. As in the context of FIG. 15, these elements are positioned on the manufacturing unit such that the front (1612), centre (1615) and rear (1618) regions of the article when in its intended use orientation (corresponding there to a front to rear orientation along a longitudinal article centre line 1610) are—at least initially—positioned cross-directionally on the manufacturing unit with the manufacturing machine direction 1620.

Once the materials are positioned appropriately, pieces of the composite corresponding to the articles are separated such as by a first separation line 1655, here shown exemplarily as a straight cross-directionally (relative to the manufacturing equipment machine direction) oriented cut line. Preferably though not necessarily thereafter, leg hoop separation lines 1667 are made, such as by conventional cut lines. There are four leg hoop separation lines 1667 for each article precursor corresponding to one article, delimiting the front and rear hoop extension regions 1712 and 1718 from the extension regions of the centre piece 1612 and 1618. Preferably, these lines are positioned for- and rear-wardly (relative to the machine direction of the manufacturing unit and the materials) of the core, but they may also be positioned in the core, provided the core provides bondable zones where these separation lines are to be positioned. These lines have a generally cross-directional orientation. Generally cross-directional orientation refers to an orientation a straight line connecting between the endpoints of a separation line has at least a cross-directions component (e.g. in a vector presentation), and preferably is angled at more than 45°, more preferably more than 60° to the manufacturing equipment machine direction The separation lines may be straight lines or curvilinearly shaped, such as shown in FIG. 16A. One end of these lines will terminate in the transition region of the centre region 1615 of the article and the front and rear regions 1612 and 1618 respectively. The other end of these lines may run into the longitudinal side margins 1660 of the web material, or may run into the first separation lines 1655.

The first separation lines 1655 may be continuous across the full CD width or discontinuous. If continuous, they completely separate adjacent hoop pieces of neighbouring products or precursors thereof. If discontinuous, the separation lines are interrupted where the leg hoop separation lines taper together. The remaining connection between a first and a second piece (corresponding to consecutives first and second articles or precursors) is preferably weak enough to be torn apart by small predetermined mechanical actions, such as downstream pullforces without another cutting action, but in any case sufficiently strong to withstand the required handling.

Once the first article (1655) and the leg hoop (1667) separation lines have been made, the materials corresponding to the centre pieces of the articles are spaced apart in the machine direction of the webs. This can be performed by conventional means (not shown), similar to those described in U.S. Pat. No. 6,544,375 or WO 06/103487. Essentially, two subsequent pieces are held to their support in the regions corresponding to the centre pieces of the article and the leg hoop extensions, whilst the supports are spaced apart. During the spacing, the leg hoops 1712 and 1718 of a first and a subsequent piece may be still connected, and held to their support, or they may be unconnected. They will rotate around z-directional axes (not shown), which are positioned where the leg hoop separation lines terminate towards the leg hoop centre piece, thus forming the front and rear leg hoop extensions 1712 and 1718). The centre hoop region 1715 will inevitably (due to geometric constraints) buckle up and invert such that its surface—indicated by the hatching in FIG. 16.B—now partly overlays the centre crotch region 1615.

After that, further process steps may be performed, in particular a web material 1750 serving as a side panel material in the article may be introduced by conventional means and techniques. Similarly, closure means for the article may be introduced, here shown exemplarily by hook patches, which may engage with nonwoven webs. Alternatively, adhesive tapes or other closure means may be introduced.

Now, the webs may be folded along a machine direction oriented folding line, such that the front and rear portions overlay. Before or thereafter, the side panels may be tucked in, such as by means as described in WO06/102974, and subsequent pieces may be fully separated along the final separation line 1669 to form the final article or precursor. In addition or alternatively to the above mentioned closure means, the side margins parallel to the longitudinal centre line of the articles may be seamed together, such as by thermo-bonding or gluing, or other means, all well known to a person skilled in the art, and they may optionally be tucked in prior to packaging.

FIG. 17 A-D shows a further process option according to the present invention for the manufacture of an article comprising a centre piece without substantially extending beyond crotch region. To this end (see FIG. 17A), centre crotch pieces 1615 are positioned MD directionally (1620) spaced apart on support means. Hoop elements 1710 are positioned such that the mid hoop regions are in registry and partly overlapping the centre crotch pieces, with their first and second extensions extending laterally outwardly (relative to the manufacturing equipment). As described above, the extensions are rotated—here shown by 90°—and the mid regions are inverted, whereby small separation lines (as indicated by cut lines 1698) allow folding of parts of the centre piece. Simultaneously, the spacing of two subsequent crotch pieces is adjusted. Side panel material 1750 may be continuously added, and optionally a 1760 core may be included in the centre piece. Upon a final separation along final separation line 1699, a complete article 1690 may further be processed, such as by adding closure means, folding, and/or packaging FIG. 18 describes a quite analogous approach, wherein, however, the hoops of two consecutive pieces are kept together at close to their side margin, i.e. by a separation line, such as a cut line 1697 not running into the side margins but stopping at the connection regions 1696. Also indicated in this figure is the option of inverting the total article or precursor before the side panels 1750 are added—here shown as FIG. 18B (pre-inverting) and FIG. 18C (post-inverting, here indicated by showing different hatching for the hoop material).

In yet a further embodiment, the rotation may also be executed by affixing the centre region of the hoop to a support plate, which is rotated by 180°, thusly inverting the centre region and rotating the first and second extension of the hoop outwardly.

The present invention allows further to readily implement a so called secondary topsheet as being particularly suitable for handling of faeces. The general principles of such "bowel movement isolation" (BMI) features are described in above referenced WO06/102974. The starting point for such a design may be the construction as shown in FIG. 10 and described herein above. FIG. 14A thus shows essentially the same features as FIG. 10, with the additional features of a secondary topsheet, a topsheet slit 1450, attachment lines 1460, and optional elastic features for the leg hoop 1470 and for the BMI topsheet slit 1480.

When the absorbent core 1060 is sufficiently encased such as by a suitable coversheet (which then may be referred to as a "first or primary topsheet"—not shown in the figures), topsheet 1050 may be slit in the area of the rear centre part which in use is positioned in close registry to the anus of the wearer, here shown as a preferred embodiment of a topsheet cut line 1450 along a longitudinal centreline. A further attachment means, such as a glue line 1460, may be applied between the topsheet surface 1350 of the centre portion of the leg hoop 1215 and the topsheet surface 1050. Additionally, the topsheet may be connected to the lateral outer part of the mid portions of the first and second web material, When the product, such as after being combined with side panels, is folded and a closed pant structure is formed (either on the wearer or pre-closed or closed at the manufacturer) upon donning, thereby also forming the 3D body conforming cup shape, the topsheet will detach from the surface of the core, and will automatically be positioned closer to the wearer, thereby creating a void space such as between the absorbent core or the backsheet and the body contacting topsheet. The slit will widen, and due to its relative positioning to the anus of the wearer allow faeces to pass through, whilst the surrounding skin of the wearer is protected by the topsheet. Optionally, leg hoop 1470 elastics may be implemented, and/or further elastics 1480 may be positioned parallel/longitudinally to the topsheet slit. It should be noted, that such a design is not readily achievable by the "flipping method" of the PCT'3844 application.

The invention claimed is:

1. Method for forming a pair of pre-forms for hoops on a high speed production line for being used in an article to be worn on a lower torso of a wearer, said article comprising a centre piece web material;

said pre-forms for said hoops comprising a centre hoop region and a first and a second extension region;

said centre piece web material a) being adapted to be positioned in a crotch region of a wearer during use by comprising a crotch region exhibiting a front and a rear margin and side margins, b) thereby defining a longitudinal in-use orientation of the article or its pre-cursor along a longitudinal article centre line during its intended use on a wearer;

c) and optionally comprising a front and/or rear region extending beyond the front and rear margins of said crotch region so as to extend towards the front and rear waist region of a wearer during use;

wherein said pre-form for said hoop and said centre piece webs extend essentially in two dimensions with a thickness dimension (z-) perpendicular thereto and exhibit a first and a second opposite surface;

said method comprising the steps of 1) providing said centre piece web material as an essentially continuous web material;

2) providing a hoop forming material a) as one or more essentially continuous web materials or cut pieces thereof b) or by separating said first and second hoop extension regions from a combined centrepiece and hoop material comprising i) said centre piece comprising said crotch region and front and rear extension regions, and ii) said centre hoop region and said front and rear hoop extension regions, iii) whereby said centre hoop region extends laterally outwardly of said centre crotch region;

iv) and whereby said first and second hoop extensions regions are separated from said front and rear extensions by hoop separation lines, optionally cut lines, sections of which extend predominantly along a longitudinal article centre line;

3) positioning or maintaining the positioning of said hoop web(s) such that a) said centre hoop regions are essentially in registry with said centre piece crotch region, each one with one of said side margins of said centre piece, b) and said front and rear hoop extension regions extend essentially parallel to said longitudinal article centre line forwardly and rearwardly of said centre hoop regions;

said method being characterized in that it further comprises the step of 4) rotating each of said front and rear hoop extension regions around a z-directionally oriented axis such that a) said extensions are oriented outwardly and away at angles of between 45° and 135° relative to said longitudinal article centre line;

b) and said hoop forming materials are partly folded over themselves such that said centre hoop region is inverted and has an opposite surface orientation than said hoop extension regions.

2. A method according to claim 1, further comprising one or more of the following steps:

5) adding materials to form side panels for diapers or pants articles;

6) adding closure means so as to allow closure of said articles;

7) adding elastification means;

8) adding secondary topsheet materials.

3. A method according to claim 1 or 2 wherein said hoop forming material is provided as one or more essentially continuous web materials or cut pieces, and wherein said rotating step 4) comprises the steps of
  i) affixing first and second extensions of said hoop material to support plates;
  ii) rotating said support plates around an essentially z-directionally oriented axis, such that said centre hoop region overlays said centre crotch region invertedly;
  iii) releasing said first and second hoop extensions from said support plates;
  iv) connecting said inverted centre hoop region to said centre crotch region.

4. A method according to claim 1, further comprising a manufacturing equipment machine direction, wherein said longitudinal article centre line and the manufacturing equipment machine direction are essentially aligned parallel.

5. A method according to claim 1, further comprising manufacturing equipment characterized by an MD direction, wherein said longitudinal article centre line and said manufacturing equipment machine direction are essentially perpendicularly arranged, further comprising the process step of
  9) increasing the spacing of two consecutive articles or precursors thereof along the MD direction of the manufacturing equipment.

6. A method according to claim 5,
  a) wherein said hoop forming material is essentially separated from a combined centrepiece and hoop material;
  b) wherein said first and second hoop extensions are separated from said front and rear centre piece extensions by separation lines, optionally cut lines, at least sections of which extend predominantly along the longitudinal article centre line;
  c) wherein said first and second leg hoop extensions are rotated;
  d) and wherein said centre hoop regions are inverted concurrently with said rotating of said extensions.

7. A method according to claim 5, wherein said hoop material of a first and a second subsequent article or precursor remain partly connected during said step 9).

8. The method of claim 1 wherein said extensions are oriented outwardly and away at angles of between 60° to 120° relative to said longitudinal article centre line.

* * * * *